(12) United States Patent
Leem et al.

(10) Patent No.: US 12,738,343 B2
(45) Date of Patent: Sep. 15, 2026

(54) ENGINEERING OF ANTIGEN-BINDING PROTEINS

(71) Applicant: Alchemab Therapeutics Ltd, London (GB)

(72) Inventors: Jinwoo Leem, London (GB); Jacob Galson, London (GB)

(73) Assignee: Alchemab Therapeutics Ltd, London (GB)

( * ) Notice: Subject to any disclaimer, the term of this patent is extended or adjusted under 35 U.S.C. 154(b) by 407 days.

(21) Appl. No.: 18/287,352

(22) PCT Filed: Apr. 14, 2022

(86) PCT No.: PCT/EP2022/060073
§ 371 (c)(1),
(2) Date: Oct. 18, 2023

(87) PCT Pub. No.: WO2022/223451
PCT Pub. Date: Oct. 27, 2022

(65) Prior Publication Data

US 2024/0203523 A1 Jun. 20, 2024

(30) Foreign Application Priority Data

Apr. 22, 2021 (GB) ...................................... 2105776

(51) Int. Cl.
*G06N 3/00* (2023.01)
*G06N 3/044* (2023.01)
(Continued)

(52) U.S. Cl.
CPC ............ *G16B 15/30* (2019.02); *G06N 3/044* (2023.01); *G16B 30/00* (2019.02); *G16B 40/20* (2019.02)

(58) Field of Classification Search
CPC ........ G16B 15/30; G16B 30/00; G16B 40/20; G16B 35/10; G16B 30/10; G16B 50/00; G06N 3/044; G06N 3/0455
See application file for complete search history.

(56) References Cited

U.S. PATENT DOCUMENTS 5,571,639 A * 11/1996 Hubbell ................ C07K 1/045 430/30
6,114,114 A * 9/2000 Seilhamer ............. G16B 35/10 702/19
(Continued)

FOREIGN PATENT DOCUMENTS

WO WO 2020/236839 A2 11/2020
WO WO 2022/223451 A1 10/2022

OTHER PUBLICATIONS

Bashford-Rogers et al., Analysis of the B cell receptor repertoire in six immune-mediated diseases. Nature. Oct. 3, 2019;574(7776):122-6.

(Continued)

*Primary Examiner* — Frank F Huang
(74) *Attorney, Agent, or Firm* — Wolf, Greenfield & Sacks, P.C.

(57) ABSTRACT

Methods of identifying an antigen-binding protein comprising a pair of chains are described. The methods comprise providing a query sequence comprising a first chain sequence, and identifying a corresponding chain sequence by providing the query sequence to a deep learning model configured to take as input a query first chain sequence and to produce as output at least one corresponding chain sequence, thereby identifying a corresponding chain sequence for the query sequence, wherein the deep learning model has been trained using training first and corresponding chain sequences from known chain pairs. The first chain sequence may be a heavy/light chain of an antibody or B cell
(Continued)

receptor or β/α/δ/γ chain of a T cell receptor, and the corresponding chain may be a light/heavy chain of an antibody or B cell receptor or an a β/α/δ/γ chain of a T cell receptor. The methods find uses in any context where it is desirable to identify chain pairings for antigen-binding molecules, such as e.g. in the context of identifying antigen-binding molecules that have a desired (e.g. therapeutic or functional) property. Related methods, systems and products are described.

20 Claims, 13 Drawing Sheets

(51) Int. Cl.

| | |
|---|---|
| ***G16B 15/30*** | (2019.01) |
| ***G16B 30/00*** | (2019.01) |
| ***G16B 40/20*** | (2019.01) |

(56) References Cited

U.S. PATENT DOCUMENTS 6,470,277 B1 * 10/2002 Chin .................... G16B 30/10 706/45
7,444,308 B2 * 10/2008 Guyon ................ G06V 10/764 706/20
7,542,854 B2 * 6/2009 Kelkar .................. G16B 25/10 706/46
7,720,614 B2 * 5/2010 Davidson .............. G16B 20/20 703/2
11,587,645 B2 * 2/2023 Amimeur .............. G06N 3/123
2002/0049542 A1 * 4/2002 Rzhetsky .............. G16B 10/00 435/6.12
2025/0391563 A1 * 12/2025 Cho ...................... G16H 50/20

OTHER PUBLICATIONS

Mason et al., Optimization of therapeutic antibodies by predicting antigen specificity from antibody sequence via deep learning. Nature Biomedical Engineering. Jun. 2021;5(6). 13 pages.
International Search Report and Written Opinion mailed Jan. 22, 2024 in connection with International Application No. PCT/EP2023/078395.
[No Author Listed], OAS Observed Antibody Space. May 25, 2022. 1 page. The Wayback Machine. URL:https://web.archive.org/web/20220525025511/https://opig.stats.ox.ac.uk/webapps/oas [retrieved on Mar. 1, 2024].
[No Author Listed], RoBERTa. Aug. 19, 2022. 96 pages. The Wayback Machine. URL:https://web.archive.org/web/20220819011413/https://huggingface.co/docs/transformers/model_doc/roberta#transformers.RobertaModel [retrieved on Mar. 1, 2024].
Brown et al., Language models are few-shot learners. Advances in neural information processing systems. 2020;33:1877-901. Including Supplementary Information. 57 pages.
Choi, Artificial intelligence for antibody reading comprehension: AntiBERTa. Patterns. Jul. 8, 2022;3(7):100535. 2 pages. doi:10.1016/j.patter.2022.100535.
Dao et al., Flashattention: Fast and memory-efficient exact attention with io-awareness. Advances in neural information processing systems. Dec. 6, 2022;35:16344-59. Including Supplementary Information. 51 pages.
Ideasbyjin, Github repository—alchemab/antiberta. GitHub. Dec. 17, 2021. URL:https://github.com/alchemab/antiberta/blob/master/antibody-tokenizer/vocab.json [retrieved on Mar. 1, 2024].
Jaffe et al., Functional antibodies exhibit light chain coherence. Nature. Nov. 2022;611(7935):352-357. Including Supplementary Information. 29 pages. doi:10.1038/s41586-022-05371-z.
Joshi et al., SpanBERT: Improving Pre-training by Representing and Predicting Spans. arXiv preprint. arXiv:1907.10529v3. Jan. 18, 2020. 13 pages.
Leem et al., Deciphering the language of antibodies using self-supervised learning. Patterns. Jul. 8, 2022;3(7):100513. 12 pages. doi:10.1016/j.patter.2022.100513.
Lin et al., A Survey of Transformers. arXiv preprint. arXiv:2106.04554v2. Jun. 15, 2021. 40 pages.
Nijkamp et al., ProGen2: Exploring the boundaries of protein language models. arXiv preprint. arXiv:2206.13517v1. Jun. 27, 2022. 20 pages.
Penedo et al., The RefinedWeb Dataset for Falcon LLM: Outperforming Curated Corpora with Web Data, and Web Data Only. arXiv preprint. arXiv:2306.01116v1. Jun. 1, 2023. 32 pages.
Press et al., Train short, test long: Attention with linear biases enables input length extrapolation. arXiv preprint. arXiv:2108.12409v1. Aug. 27, 2021. 23 pages.
Prihoda et al., BioPhi: A platform for antibody design, humanization, and humanness evaluation based on natural antibody repertoires and deep learning. MAbs. Jan.-Dec. 2022;14(1):2020203. 16 pages. doi: 10.1080/19420862.2021.2020203.
Ramachandran et al., Searching for activation functions. arXiv preprint. arXiv:1710.05941v2. Oct. 27, 2017. 13 pages.
Safari et al., Self-Attention Encoding and Pooling for Speaker Recognition. arXiv preprint. arXiv:2008.01077v1. Aug. 3, 2020. 5 pages.
Shaw et al., Self-Attention with Relative Position Representations. arXiv preprint. arXiv:1803.02155v2. Apr. 12, 2018. 5 pages.
Steinegger et al., Clustering huge protein sequence sets in linear time. Nat Commun. Jun. 29, 2018;9(1):2542. Including Supplementary Information. 13 pages. doi:10.1038/s41467-018-04964-5.
Su et al., Roformer: Enhanced transformer with rotary position embedding. arXiv preprint. arXiv:2104.09864v1. Apr. 20, 2021. 12 pages.
Touvron et al.,. Llama 2: Open Foundation and Fine-Tuned Chat Models. arXiv preprint. arXiv:2307.09288v2. 77 pages.
Weber et al., immuneSIM: tunable multi-feature simulation of B- and T-cell receptor repertoires for immunoinformatics benchmarking. Bioinformatics. Jun. 1, 2020;36(11):3594-3596. Including Supplementary Data. 29 pages. doi:10.1093/bioinformatics/btaa158.
Search Report for British Application No. 2105776.5 dated Jan. 24, 2022.
International Search Report and Written Opinion for International Application No. PCT/EP2022/060073 mailed Jun. 30, 2022.
International Preliminary Report on Patentability for International Application No. PCT/EP2022/060073 mailed Nov. 2, 2023.
Bahdanau et al., Neural machine translation by jointly learning to align and translate. arXiv preprint arXiv:1409.0473v7. May 19, 2016. 15 pages.
Carter et al., Single T cell sequencing demonstrates the functional role of αβ TCR pairing in cell lineage and antigen specificity. Frontiers in Immunology. Jul. 31, 2019;10:1516. 14 pages.
Child et al., Generating long sequences with sparse transformers. arXiv preprint arXiv:1904.10509. Apr. 23, 2019. 10 pages.
Chung et al., Empirical evaluation of gated recurrent neural networks on sequence modeling. arXiv preprint arXiv:1412.3555. Dec. 11, 2014. 9 pages.
Dekosky et al., High-throughput sequencing of the paired human immunoglobulin heavy and light chain repertoire. Nature biotechnology. Feb. 2013;31(2):166-9.
Dekosky et al., In-depth determination and analysis of the human paired heavy-and light-chain antibody repertoire. Nature medicine. Jan. 2015;21(1):86-91.
Dekosky et al., Large-scale sequence and structural comparisons of human naive and antigen-experienced antibody repertoires. Proceedings of the National Academy of Sciences. May 10, 2016;113(19):E2636-45.
Devlin et al., BERT: Pre-training of Deep Bidirectional Transformers for Language Understanding. Proceedings of NAACL-HLT 2019:4171-86.
Dunbar et al., ANARCI: antigen receptor numbering and receptor classification. Bioinformatics. Jan. 15, 2016;32(2):298-300.
Eccles et al., T-bet+ memory B cells link to local cross-reactive IgG upon human rhinovirus infection. Cell reports. Jan. 14, 2020;30(2):351-66.

(56) References Cited

OTHER PUBLICATIONS

Furcy et al., Limited discrepancy beam search. IJCAI. Jul. 30, 2005. 7 pages.
Galson et al., Deep sequencing of B cell receptor repertoires from COVID-19 patients reveals strong convergent immune signatures. Frontiers in immunology. Dec. 15, 2020;11:605170.
Glanville et al., Precise determination of the diversity of a combinatorial antibody library gives insight into the human immunoglobulin repertoire. Proceedings of the National Academy of Sciences. Dec. 1, 2009;106(48):20216-21.
Howie et al., High-throughput pairing of T cell receptor α and β sequences. Science translational medicine. Aug. 19, 2015;7(301):301ra131-. 19 pages.
Hsiao et al., Immune repertoire mining for rapid affinity optimization of mouse monoclonal antibodies. MAbs May 19, 2019;11(4):735-46.
Jayaram et al., Germline VH/VL pairing in antibodies. Protein Engineering, Design & Selection. Oct. 1, 2012;25(10):523-30.
Ji et al., DNABERT: pre-trained Bidirectional Encoder Representations from Transformers model for DNA-language in genome. bioRxiv. Sep. 19, 2020:2020-09. 22 pages.
King et al., Single-cell analysis of human B cell maturation predicts how antibody class switching shapes selection dynamics. Science Immunology. Feb. 12, 2021;6(56):eabe6291. 16 pages.
Kovaltsuk et al., Observed antibody space: a resource for data mining next-generation sequencing of antibody repertoires. The Journal of Immunology. Oct. 15, 2018;201(8):2502-9.
Krawczyk et al., Looking for therapeutic antibodies in next-generation sequencing repositories. MAbs Oct. 3, 2019;11(7): 1197-1205.
Leem et al., ABodyBuilder: Automated antibody structure prediction with data-driven accuracy estimation. MAbs Oct. 2, 2016; 8(7): 1259-68.
Ling et al., Effect of VH-VL families in Pertuzumab and Trastuzumab recombinant production, Her2 and FcγIIA binding. Frontiers in immunology. Mar. 12, 2018;9:469. 32 pages.
Liu et al., Roberta: A robustly optimized BERT pretraining approach. arXiv preprint arXiv:1907.11692. Jul. 26, 2019. 13 pages.
Mora et al., How many different clonotypes do immune repertoires contain?. Current Opinion in Systems Biology. Dec. 1, 2019;18:104-10.
Nielsen et al., Human B cell clonal expansion and convergent antibody responses to SARS-CoV-2. bioRxiv. Jul. 9, 2020:2020-07. 29 pages.
Radford et al., Language models are unsupervised multitask learners. OpenAI blog. Feb. 24, 2019;1(8):9. 17 pages.
Rakocevic et al., The landscape of high-affinity human antibodies against intratumoral antigens. bioRxiv. May 2021. 23 pages.
Raybould et al., Public Baseline and shared response structures support the theory of antibody repertoire functional commonality. PLoS computational biology. Mar. 1, 2021;17(3):e1008781. 23 pages.
Reddy et al., Monoclonal antibodies isolated without screening by analyzing the variable-gene repertoire of plasma cells. Nature biotechnology. Sep. 2010;28(9):965-9.
Rees, Understanding the human antibody repertoire. Mabs. Jan. 1, 2020;12(1): 1729683. 17 pages.
Richardson et al., A computational method for immune repertoire mining that identifies novel binders from different clonotypes, demonstrated by identifying anti-pertussis toxoid antibodies. MAbs Jan. 1, 2021;13(1): 1869406. 27 pages.
Rothe et al., Leveraging Pre-trained Checkpoints for Sequence Generation Tasks. arXiv preprint arXiv:1907.12461. Apr. 16, 2020. 17 pages.
Saka et al., Antibody design using LSTM based deep generative model from phage display library for affinity maturation. Scientific reports. Mar. 12, 2021;11(1):5852. 16 pages.
Seeliger et al., Boosting antibody developability through rational sequence optimization. MAbs. 2015;7(3):505-15.
Setliff et al., High-throughput mapping of B cell receptor sequences to antigen specificity. Cell. Dec. 12, 2019;179(7):1636-46.
Simonich et al., Kappa chain maturation helps drive rapid development of an infant HIV-1 broadly neutralizing antibody lineage. Nature Communications. May 16, 2019;10(1):2190. 27 pages.
Sutskever et al., Sequence to Sequence Learning with Neural Networks. arXiv preprint arXiv:1409.3215. Dec. 14, 2014. 9 pages.
Teplyakov et al., Structural diversity in a human antibody germline library. mAbs;8(6):1045-1063.
Tiller et al., A fully synthetic human Fab antibody library based on fixed VH/VL framework pairings with favorable biophysical properties. MAbs May 1, 2013;5(3):445-70.
Vander Heiden et al., Dysregulation of B cell repertoire formation in myasthenia gravis patients revealed through deep sequencing. The Journal of Immunology. Feb. 15, 2017;198(4):1460-73.
Vaswani et al., Attention Is All You Need. arXiv:1706.03762. Aug. 2, 2023. 15 pages.
Warszawski et al., Optimizing antibody affinity and stability by the automated design of the variable light-heavy chain interfaces. PLoS computational biology. Aug. 23, 2019;15(8):e1007207. 24 pages.
Wolf et al., HuggingFace's transformers: State-of-the-art natural language processing. arXiv:1910.03771. Jul. 14, 2020. 8 pages.
Xiong et al., On Layer Normalization in the Transformer Architecture. arXiv:2002.04745. Jun. 29, 2020. 17 pages.
Ye et al., IgBLAST: an immunoglobulin variable domain sequence analysis tool. Nucleic acids research. Jul. 1, 2013;41(W1):W34-40.
Zheng et al., Massively parallel digital transcriptional profiling of single cells. Nature communications. Jan. 16, 2017;8(1):14049. 30 pages.
Zhou et al., Beam-Stack Search: Integrating Backtracking with Beam Search. ICAPS Jun. 5, 2005:90-8.
Zhu et al., Mining the antibodyome for HIV-1-neutralizing antibodies with next-generation sequencing and phylogenetic pairing of heavy/light chains. Proceedings of the National Academy of Sciences. Apr. 16, 2013;110(16):6470-5.

* cited by examiner

ENGINEERING OF ANTIGEN-BINDING PROTEINS

RELATED APPLICATIONS

This application is a national stage filing under 35 U.S.C. § 371 of international application number PCT/EP2022/060073, filed Apr. 14, 2022, which claims the benefit of British application number GB 2105776.5, filed Apr. 22, 2021, each of which is incorporated by reference in its entirety.

FIELD OF THE INVENTION

The present invention relates to methods for engineering antigen-binding proteins such as B cell receptors, antibodies and T cell receptors by identifying variable chain pairings from single input variable chains, such as a heavy-light chain pair from an input heavy or light chain, or an α-β chain pair from an input α or β chain. The present invention also relates to methods of providing an antigen-binding protein, such as a therapeutic antibody, derived from an input variable chain, for example a B cell receptor/antibody heavy or light chain.

BACKGROUND TO THE INVENTION

Effective humoral immunity requires a great diversity of B cells capable of binding different antigens through their B cell receptor (BCR). The theoretical total size of the BCR repertoire in humans is estimated to be up to $\sim 10^{15}$ variants, of which $\sim 10^{9}$ are in circulation in a single individual at any time [Rees, 2020]. BCRs are comprised of two pairs of two protein chains: two heavy chains and two light chains. Each B cell expresses a (likely unique) pair of heavy and light chains to form its BCR, which is expressed on its surface, or secreted as an antibody. Over 600 million different human heavy chain sequences and approximately 70 million light chain sequences are currently catalogued in the Observed Antibody Space [Kovaltsuk et al., 2018]. Characterising the ensemble of BCRs of an individual (also referred to as an individual's BCR repertoire), has proven to be a valuable tool for understanding the biology of various diseases [Vander Heiden et al., 2017; Bashford-Rogers et al, 2019; Nielsen et al., 2020; Simonich et al., 2019] and discovering novel therapeutic antibody drugs [Krawczyk et al., 2019; Galson et al., 2020].

There are two main approaches to characterise the BCR repertoire of an individual: single B cell sequencing, and sequencing of bulk B cell populations. Single-cell sequencing is more commonly employed for antibody discovery applications, as it preserves the pairing information between the heavy and the light chains. However, single-cell sequencing has a limited throughput, and different platforms and protocols vary in their coverage of the BCR repertoire present within a single sample. Even the most advanced microfluidic systems can typically only recover the sequences for $\sim 10^{4}$ B cells per sample [King et al., 2021; Eccles et al., 2020; Setliff et al., 2019]. Humans typically have $\sim 10^{6}$ B cells per millilitre of blood [Mora and Walczak, 2019], meaning that single-cell approaches are not capable of characterising the full B cell diversity of even small samples. Additionally, single-cell sequencing has very specific sample requirements (for example, the cells typically have to remain viable until processed, thus requiring fresh samples processed on the day of collection, or frozen according to a specific protocol), very high costs per sample compared to bulk sequencing (single-cell sequencing being at least an order of magnitude more expensive than bulk sequencing) and requires dedicated laboratory equipment.

Sequencing of bulk B cell populations can more readily recover $\sim 10^{7}$ B cell sequences per sample [Briney et al., 2019], which is significantly closer to the expected diversity in an individual. However, as B cells are lysed during library preparation, heavy-light chain pairing information is not preserved. Typically, these bulk BCR sequencing approaches focus only on the heavy chain, as it plays the dominant role in antigen binding and is much more diverse than the light chain repertoire [Kovaltsuk et al., 2018]. However, for antibody discovery, it is necessary to have both the heavy and light chain of an antibody so that it can be synthesised and functionally characterised. The gap in light chain pairing information has prompted the development of computational pairing methods [Reddy et al., 2010, Zhu et al., 2013, Raybould et al., 2021, Rakocevic et al., 2021]. However, these are limited to specific datasets and a few particular sequences within these datasets.

Similarly, cellular immunity requires a great diversity of T cells capable of binding different antigens through their T cell receptor (TCR). The total size of the TCR repertoire in humans is estimated to comprise up to $\sim 10^{15}$ unique αβ T cell receptor (TCR) pairs [Carter et al., 2019]. While experimental approaches for paired αβ TCR sequencing have been developed (including single cell approaches [Zheng et al., 2017] and multi-cell deconvolution based approaches [Howie et al., 2015]), these remain specialised and limited in throughput. Thus, the majority of the TCR repertoire knowledge available is based on bulk-sequencing on single chain repertoires, mostly the β chain repertoire. This is inherently limited especially as it has been shown that both the α and β TCR chains are involved in alloreactivity and antigen specificity [Carter et al., 2019].

Thus, there is still a need for improved methods for identifying chain pairs such as BCR heavy-light chain pairs or TCR as chain pairs, from data that does not contain this pairing information.

SUMMARY OF THE INVENTION

The problem of identifying BCR heavy-light chain pairs is far from trivial. Indeed, the diversity of the BCR repertoire results in a large search space. Additionally, while several heavy-light chain combinations can yield stable BCRs (an observation that has led some to speculate that pairing could be random [Glanville et al., 2009; Jayaram et al., 2012; DeKosky et al., 2016]), only a limited number of pairings produce functional BCRs that are capable of binding their target antigen [Teplyakov et al., 2016; Ling et al., 2018]. This indicates that functional pairing is non-random but that the determinants of functional pairings are obscured by the number of pairings that may be stable despite being non-functional. In practice, this means that finding the correct light chain is challenging even if stable pairs could be predicted, as these would produce a significant number of solutions that require experimental validation and that would be expected to poorly validate if selected primarily based on stability.

Multiple different computational approaches have been suggested, each of which have several significant drawbacks. A first approach was based on matching the relative frequencies of BCR heavy and light chains when sequenced independently [Reddy et al., 2010]. In this study, mice were first immunised to generate a strong immune response, and then the top 4-5 most frequent heavy and light chains were chosen to pair. Beyond these top 4-5 sequences, pairing based on relative frequency was not possible. More recently, Rakocevic et al. [2021] showed that the approach only worked when the sample was dominated by a small number of high frequency B cells. Zhu et al. [2013] proposed a method termed phylogenetic pairing, which involves comparing architectures of phylogenetic trees generated from heavy and light chain sequence data. This method is limited to the examination of specific clonal expansions; in this case, known antiviral antibody lineages, rather than the entire BCR repertoire. Raybould et al. [2021] proposed an approach based on pairing structural models of heavy and light chains in silico. The approach is inherently limited by the restricted and heavily skewed availability of high-quality structural templates, and can at most identify features related to stability which do not necessarily translate to functionality. Further, the approach was only able to pair families of similar sequences rather than specific sequences (which would limit its practical applicability—which has not been validated experimentally). Thus, the present inventors have identified that current methods for computational heavy-light chain pairing are therefore limited in that they only apply to specific datasets and sequences within these datasets. Indeed, any validated approach that exists are only applicable to datasets where both heavy and light chain sequences are available from the sample, where the data is dominated by large clonal expansions, and only facilitate pairing of a limited number of sequences within these datasets.

The present inventors further identified that for generalised application to antibody discovery, it is desirable to be able to generate a viable light chain for any given heavy chain. It is further desirable to be able to generate this using only heavy chain information as BCR repertoire bulk sequencing efforts often focus limited resources on sequencing the heavy chain, which is believed to play a more important functional role than the light chain. In order to tackle these problems, the present inventors postulated that it would be possible to use deep learning methods inspired by recent advances in natural language processing (NLP). Specifically, they framed the problem of identifying the native light chain sequence as a neural machine translation (NMT) problem, using Transformers [Vaswani et al., 2017] as well as other alternative deep learning architectures. Transformers have shown state-of-the-art results in a wide range of NLP tasks [Vaswani et al., 2017; Devlin et al., 2019; Liu et al., 2019; Rothe et al., 2020]. Thus, the inventors devised a method using a Transformer model (termed 'Matchmaker') that generates light chains using only the BCR heavy chain as input. On multiple blind tests of single-cell datasets with known pairings, they showed that Matchmaker provides more correct light chain gene annotations than four other methods. They then validated their predictions on a set of 9 therapeutic antibodies with known targets, and 18 heavy chains from COVID-19 patients, commonly found in diseased individuals. All Matchmaker-generated antibodies were successfully expressed, and were stable; in addition, 3 out of 9 predictions for the therapeutic antibodies and 9 of 18 predictions for the COVID-19 antibodies showed signs of binding to their target antigen in vitro. They further showed that the approach could be expanded by using a tandem transformer to "learn the language" of the single chain sequences in a pre-training step. The approach offers a novel solution to light chain pairing, and a route to fill the gaps of bulk heavy chain sequencing.

The inventors further identified that the same approach could be used to solve the problem of αβ TCR chain pairing.

Thus, according to a first aspect, there is provided a method of identifying an antigen-binding protein comprising a pair of chains, the method comprising: providing a query sequence comprising a first chain sequence, and identifying a corresponding chain sequence by: providing the query sequence to a deep learning model configured to take as input a query first chain sequence and to produce as output at least one corresponding chain sequence, thereby identifying a corresponding chain sequence for the query sequence, wherein the deep learning model has been trained using training first and corresponding chain sequences from known chain pairs. The method may have one or more of the following features.

The pair of chains may be referred to as "variable chains". The wording "known chain pairs" refers to pairs of variable chain sequences that are known to be present in antigen-binding proteins showing a desired antigen binding function, or in antigen-binding proteins that form part of at least one subject's B cell or T cell repertoire. The latter may also be referred to as "native" chain pairs.

The antigen-binding protein may comprise a heavy-light chain pair, wherein the first chain sequence is a heavy chain sequence or a light chain sequence, and the corresponding chain sequence is a light chain sequence or a heavy chain sequence. The first chain sequence may be a heavy chain sequence and the corresponding sequence may be a light chain sequence. The antigen-binding protein may be a B cell receptor or antibody, or a protein derived therefrom. Thus, the antigen-binding protein may comprise a heavy-light chain pair. The query sequence may comprise a heavy chain sequence or a light chain sequence. The corresponding chain sequence may be a light chain sequence or a heavy chain sequence.

The antigen-binding protein may comprise an αβ chain pair, wherein the first chain sequence is a β chain sequence or an α chain sequence, and the corresponding chain sequence is an α chain sequence or a β chain sequence. The first chain sequence may be a β chain sequence and the corresponding sequence is an α chain sequence. The antigen-binding protein may comprise a γδ chain pair, wherein the first chain sequence is a δ chain sequence or a γ chain sequence, and the corresponding chain sequence is a γ chain sequence or a δ chain sequence. The first chain sequence may be a δ chain sequence and the corresponding sequence may be a γ chain sequence. The antigen-binding protein may be a T cell receptor or a protein derived therefrom. Thus, the antigen-binding protein may comprise an αβ chain pair or a γδ chain pair. Thus, the query sequence may comprise a β or δ chain sequence or an α or γ chain sequence. The corresponding chain sequence may be an α or γ chain sequence or a β or δ chain sequence.

The deep learning model may be a sequence-to-sequence model. The deep learning model may comprise a recurrent neural network or a transformer. The deep learning model may be a sequence-to-sequence transformer-based model. The recurrent neural network may be a gated recurrent unit (GRU)-based model or a long short-term memory (LSTM) model. For example, a GRU-based model may comprise a GRU-based encoder and a GRU-based decoder. The encoder may be a 4-layer bi-directional GRU, for example with a hidden dimension of 1024, The decoder may be a 4-layer, forward-only GRU, for example with a hidden dimension of 1024. A transformer is a deep learning model that uses the mechanism of attention. The transformer-based model may be a transformer model with an architecture using self-attention and point-wise, fully connected layers for both the encoder and the decoder. The encoder and/or the decoder may be composed of a stack of 4 identical layers. Each layer of the encoder may have two sublayers: a multi-head self-attention layer and a position-wise fully connected feed forward network layer. Each layer of the decoder may have three sublayers: a self-attention sublayer, a layer that performs multi-head attention over the output of the encoder stack, and a feedforward network layer. The model may have a feed-forward dimension of 1024.

The deep learning model may be configured to produce as output one or more corresponding chain sequences. Each corresponding chain sequence may be associated with a confidence metric such as a probability. A corresponding chain sequence for the query sequence may be identified as a sequence of the one or more corresponding chain sequences that is associated with the highest confidence metric amongst the one or more corresponding chain sequences. The deep learning model may be configured to produce as output a single corresponding chain sequence. The deep learning model may be configured to predict each chain in a sequential manner. In other words, the deep learning model may be configured to provide predictions in a greedy manner. The deep learning model may be configured to predict chains using a beam search approach or a related approach such as beam stack search [Zhou & Hansen, 2005] and depth-first beam search [Furcy & Koenig, 2005]. The deep learning model may be configured to produce as output a plurality of corresponding chain sequences. Each of the plurality of corresponding chain sequence may be associated with a confidence metric such as a probability. The single corresponding chain sequence associated with the highest confidence metric may be reported. Thus, the method may comprise identifying a corresponding chain sequence as one of a plurality of corresponding chain sequences that is associated with the highest confidence metric amongst the one or more corresponding chain sequences. Alternatively, all corresponding chain sequences that have been predicted may be reported, advantageously together with an associated confidence metric. Alternatively, all corresponding chain sequences that have been predicted and that satisfy one or more further criteria may be reported. For example, any corresponding chain sequences that have been predicted and that have an associated confidence metric within a predetermined range from the corresponding chain sequence that is associated with the highest confidence metric may be reported.

The training first and corresponding chain sequences from known chain pairs may comprise paired training heavy and light chain sequences from single B cell sequencing data. The training data may comprise one or more datasets each previously obtained by single B cell sequencing of samples obtained from subjects or by sequencing of libraries derived therefrom. The training data may further comprise paired training heavy and light chain sequences from known antibodies/B cell receptors. For example, the training data may comprise paired training heavy and light chain sequences from one or more antibody/BCR databases, from one or more known therapeutic antibodies/BCRs, and/or from one or more antibodies/BCRs that are known to have a desired binding function.

The training data may comprise paired training heavy and light chain sequences from naïve B cell receptor libraries. The training data may comprise paired training heavy and light chain sequences from antigen-experienced B cell receptor libraries. Thus, the training data may comprise paired training heavy and light chain sequences obtained from subjects that have been exposed to one or more specific antigens.

The training first and corresponding chain sequences from known chain pairs may comprise paired training α and β chain sequences from single T cell sequencing data. The training data may comprise one or more datasets each previously obtained by single T cell sequencing of samples obtained from subjects or by sequencing of libraries derived therefrom. The training data may further comprise paired training first and corresponding chain sequences from known T cell receptors. For example, the training data may comprise paired training α and β chain sequences from one or more T cell receptor databases, from one or more known therapeutic TCRs, and/or from one or more TCRs that are known to have a desired binding function. The training data may comprise paired training α and β (or δ and γ) chain sequences from naïve T cell receptor libraries. The training data may comprise paired training α and β (or δ and γ) chain sequences from antigen-experienced T cell receptor libraries. Thus, the training data may comprise paired training α and β (or δ and γ) chain sequences obtained from subjects that have been exposed to one or more specific antigens.

The training first and corresponding chain sequences from known chain pairs may comprise paired training chain sequences wherein each pair comprises a chain sequence that comprises or consists of: a V-gene sequence or identifier, a J-gene sequence or identifier, and a junction sequence, and optionally a D-gene sequence or identifier. The training first and corresponding chain sequences from known chain pairs may comprise paired training chain sequences wherein each pair comprises a chain sequence that comprises or consists of: a chain sequence that comprises or consists of: a V-gene sequence or identifier, a J-gene sequence or identifier, and a junction sequence. The training data may comprise at least 80,000, at least 100,000, at least 120,000 or at least 150,000 pairs of training sequences, for example training heavy and light chain sequences. Advantageously, the training data may comprise at least 150,000 pairs of training heavy and light chain sequences. The training data may comprise mammalian, such as e.g. human pairs of chain sequences. The training data may comprise mammalian heavy and/or light chain sequences. The training data may comprise human heavy and/or light chain sequences. The training data may comprise training pairs of sequences from the same species as the query sequence. The training data may comprise at least 50%, at least 60%, at least 70%, at least 80%, at least 90%, or at least 95% sequences from the same species as the query sequence. The query sequence may be a sequence that is not present in the training data. The query sequence may be a sequence that has been obtained from a sample from a subject that has a desired characteristic, such as a desired phenotype. For example, the subject may have a particular clinical characteristic.

The training data may further comprise unpaired training first and/or corresponding sequences. This will be described further below. The unpaired training first and/or corresponding chain sequences may have any of the features of sequences described in relation to the paired sequences. In particular, the unpaired chain sequences may be the same type of sequences as the paired sequences (e.g. where the paired training sequences are heavy and light chain pairs, the unpaired training first/corresponding chain sequences may comprise unpaired heavy and/or light chains), may comprise sequences from the same organisms (e.g. may comprise mammalian and/or human sequences, may comprise sequences from one or more organisms, may comprise sequences from naïve libraries and/or antigen exposed libraries, etc.), may comprise the same information (such as e.g. gene segments identifiers, sequences and combinations thereof). The unpaired training sequences may comprise some or all of the first and/or corresponding sequences that are present in the paired training sequences. Advantageously, the unpaired training sequences may comprise more first chain sequences and/or more corresponding chain sequences than the paired training chain sequences. The use of additional unpaired training sequences may be particularly advantageous in embodiments where the deep learning model is a transformer-based model comprising an encoder that has been pre-trained using unpaired training first and/or light corresponding sequences and a decoder that has been pre-trained using unpaired training corresponding and/or first chain sequences.

The query chain sequence may comprise or consist of: a V-gene sequence or identifier, a J-gene sequence or identifier, and a junction sequence, and optionally a D-gene sequence or identifier. The corresponding chain sequence may comprise or consist of: a V-gene sequence or identifier, a J-gene sequence or identifier, and a junction sequence. The query chain sequence may comprise or consist of: a V-gene sequence or identifier, a J-gene sequence or identifier, and a junction sequence. The corresponding chain sequence comprises or consists of: a V-gene sequence or identifier, a J-gene sequence or identifier, and a junction sequence, and optionally a D-gene sequence or identifier. The format of the query and corresponding chain sequences is related to the format of training chain sequences. Thus, a deep learning model that has been trained using training chain sequences comprising or consisting of: a V-gene sequence or identifier, a J-gene sequence or identifier, and a junction sequence, and optionally a D-gene sequence or identifier, may accept as input or produce as output a chain sequence comprising or consisting of these components. Similarly, a deep learning model that has been trained using training chain sequences comprising or consisting of: a V-gene sequence or identifier, a J-gene sequence or identifier, and a junction sequence, may accept as input or produce as output a chain sequence comprising or consisting of these components. The query sequence may comprise or consist of one or more first chain CDR sequence(s). The corresponding sequence may comprise or consist of one or more corresponding chain CDR sequence(s), optionally wherein the query/corresponding sequence comprises or consists of a CDR3 sequence.

All sequences may be amino acid sequences. Providing the query sequence to the deep learning model may comprises encoding the query sequence using an encoding scheme wherein each gene sequence identifier corresponds to an individual token. Providing the query sequence to the deep learning model may comprises encoding the query sequence using an encoding scheme wherein each amino acid corresponds to an individual token. Providing the query sequence to the deep learning model may comprises encoding the query sequence using an encoding scheme wherein sequences (i.e. sequences that are available as full sequences rather than gene identifiers) are encoded using tokens that each correspond to an individual k-mer or using byte-pair encoding. Each sequence may be encoded using overlapping k-mers. The k-mers may be of length 1 to 5. The k-mers may be of fixed length. For example, a fixed k-mer length of 1, 2, 3, 4 or 5 may be used. A k-mer of length 1 is equivalent to encoding each character (e.g. each amino acid) individually. A k-mer of length k>2 (such as e.g. 3) may be used as part of an encoding scheme that uses overlapping or non-overlapping k-mers. Overlapping k-mers may overlap by different extents. For example, k-mers of length 3 may overlap by 1 or 2 characters. In a scheme using a k=3, each token corresponds to a unique set of 3 characters (e.g. a motif of 3 amino acids). Identifying the corresponding chain sequence may comprise decoding a corresponding sequence output by the deep learning model using an encoding scheme wherein each gene sequence identifier corresponds to an individual token. Identifying the corresponding chain sequence may comprise decoding a corresponding sequence output by the deep learning model using an encoding scheme wherein each amino acid corresponds to an individual token. Identifying the corresponding chain sequence may comprise decoding a corresponding sequence output by the deep learning model using an encoding scheme wherein sequences are encoded using tokens that each correspond to an individual k-mer or using byte-pair encoding. Each sequence may be encoded using overlapping k-mers. The encoding scheme may have been previously defined based on the content of the training chain sequences. The encoding scheme may have been defined based on the content of the training chain sequences, wherein tokens are excluded from the vocabulary constructed based on the content of the training chain sequences if they are used a number of times below a predetermined threshold (e.g. 2) in the training data (separately or jointly for the first and corresponding chain sequences in the paired training data). The encoding scheme may have been previously defined based on the content of the training chain sequences by constructing a vocabulary separately for the training first chains and for the training corresponding chains in the training data.

The training data may have been filtered to exclude any pairs comprising a junction sequence (in the first and/or corresponding chain) that is outside of a predetermined range of lengths. In other words, the training data may not comprise any pairs comprising a first (e.g. heavy) chain junction that is outside of a predetermined range of lengths and/or a corresponding (e.g. light) chain junction that is outside of a predetermined range of lengths. For example, pairs comprising a heavy chain junction sequence below a predetermined length, such as e.g. 3, 4, 5, 6, 7, 8, 9 or 10 amino acids, may have been excluded. As another example, pairs comprising a heavy chain junction sequence above a predetermined length, such as e.g. 25, 26, 27, 28, 29, 30, 31, 32, 33, 34, or 35 amino acids, may have been excluded. As another example, pairs comprising a light chain junction sequence below a predetermined length, such as e.g. 3, 4, 5, 6, 7, 8, 9 or 10 amino acids, may have been excluded. As another example, pairs comprising a light chain junction sequence above a predetermined length, such as e.g. 15, 16, 17, 18, 19, 20, 20, 21, 22, 23, 24, 25, 26, 27, 28, 29, or 30 amino acids, may have been excluded. The predetermined length may be the same or different for the junction sequences in the corresponding (e.g light) chain and in the first (e.g. heavy) chain of a pair. In a specific example, pairs comprising a heavy chain junction sequence of fewer than 7 amino acids may have been excluded and/or pairs comprising a heavy chain junction sequence of more than 30 amino acids may have been excluded. Instead or in addition to this, pairs comprising a light chain junction sequence of fewer than 7 amino acids may have been excluded and/or pairs comprising a light chain junction sequence of more than 20 amino acids may have been excluded.

The query sequence and/or the corresponding sequence may comprise one or more gene sequence identifiers and the method may further comprise replacing the one or more gene sequence identifiers by the corresponding germline sequence.

The deep learning model may be a transformer-based model comprising an encoder that has been pre-trained using unpaired training first and/or corresponding chain sequences and a decoder that has been pre-trained using unpaired training corresponding and/or first chain sequences. The encoder and/or the decoder may comprise a BERT model or a variant thereof, such as e.g. BERT, RoBERTa, or DistilBERT, and/or an autoregressive transformer model, such as GPT-2. The encoder and/or the decoder may comprise a RoBERTa model, a BERT model and/or a GPT-2 model. The encoder and decoder may comprise the same model. The encoder and decoder may both comprise models trained using unpaired training corresponding and first chain sequences. For example, the encoder and decoder may both comprise models trained using random pairs each comprising a first and corresponding chain sequence. Alternatively, the encoder may comprise a model trained using training first (e.g. heavy or light) chain sequences, and the decoder may comprise a model trained using corresponding (e.g. light or heavy) chain sequences. When the encoder and decoder both comprise models trained using unpaired training first and corresponding chain sequences, the encoder and decoder may both comprise the same pre-trained model. Thus, the encoder and decoder may be initialised using pre-trained models that have the same architecture with the same parameters. The unpaired training chain sequences may comprise full length sequences for the variable region of the corresponding chain. The unpaired training chain sequences may comprise full sequences for the variable region of the first chain. The transformer-based model may have been trained using paired first and corresponding (e.g. heavy and light) chain sequences from known chain pairs, wherein said sequences do not comprise full length sequences for the variable region of the corresponding chain and/or the first chain. In such embodiments, the transformer-based model may have been trained by obtaining paired training sequences that comprise full length sequences for the variable region of the corresponding chain and/or the first chain by imputing missing sequence information.

Imputing missing sequence information may comprise replacing a gene identifier by the corresponding germline sequence. Imputing missing sequence information may comprise using the pre-trained encoder and/or the pre-trained decoder (for example depending on the chain for which missing sequence information is imputed) to predict a full-length sequence from each of the paired training first (e.g. heavy) and/or corresponding (e.g. light) chain sequences. Alternatively, the unpaired training corresponding (e.g. light) chain sequences and/or the unpaired training first (e.g. heavy) chain sequences may have been converted to a format that matches the format of the respective paired training sequences prior to training the encoder and/or the decoder.

Providing a query sequence may comprise obtaining the query sequence from a user through a user interface, from a computing device, from a sequence acquisition means or a computing device associated with a sequence acquisition means, from a database or other computer readable medium. Providing a query sequence may comprise sequencing a sample comprising genetic material encoding for an antigen-binding molecule comprising the query sequence. Obtaining the query sequence may comprise performing B cell bulk sequencing of a sample comprising B cells, T cell bulk sequencing of a sample comprising T cells, or bulk sequencing of a sample comprising any other cells expressing an antigen-binding molecule comprising the query sequence, or genetic material derived therefrom, such as a B cell receptor library or a T cell receptor library. Providing a query sequence may comprise obtaining a sample comprising B cells, T cells or other cells expressing an antigen-binding molecule comprising the query sequence, or genetic material derived therefrom, such as a B cell receptor library or T cell receptor library. Providing a query sequence may comprise sequencing a sample comprising genetic material encoding for an antigen-binding molecule comprising the query sequence, for example by performing B cell bulk sequencing of a sample comprising B cells (or any other cells expressing an antigen-binding molecule comprising the query sequence, or genetic material derived therefrom, such as a B cell receptor library). Providing a query sequence may comprise obtaining a sample comprising B cells, or other cells expressing an antigen-binding molecule comprising the query sequence, or genetic material derived therefrom, such as a B cell receptor library.

The method may further comprise providing the identified corresponding sequence, a part thereof or information derived therefrom, to a user through a user interface.

According to a second aspect, there is provided a method of providing antigen-binding protein chain pairings for a plurality of query sequences comprising a first chain sequence, the method comprising: performing the method of any embodiment of the first aspect for each of the query sequences. The plurality of query sequences may be heavy or light chain sequences obtained by bulk B cell repertoire sequencing. The plurality of query sequences may comprise at least 100, at least 1000, at least 10,000, or at least 100,000 sequences. The plurality of query sequences may have been obtained by bulk B cell sequencing of the heavy or light chain repertoire in a sample, such as a sample from a subject. The plurality of sequences may be a subset of a set of sequences obtained by bulk B cell sequencing of the heavy or light chain repertoire in a sample. The method according to the present aspect may have any of the features described in relation to the first aspect.

According to a third aspect, there is provided a method of providing an antigen-binding protein having a desired property, the method comprising: providing one or more query sequences comprising a first chain sequence, wherein at least one of the one or more query sequences is likely to have the desired property, and identifying a corresponding chain sequence for each of the one or more query sequences using the method of any embodiment of the first aspect. The method may have any one or more of the following features.

The method may further comprise obtaining one or more candidate antigen-binding proteins each comprising one of the query sequences and the corresponding sequence or sequences derived therefrom. The method may further comprise testing the one or more candidate antigen-binding proteins for the desired property. The method of the present aspect may have any of the features described in relation to the first or second aspects. The one or more candidate antigen-binding proteins may be antibodies or fragment thereof. Sequences derived from an identified chain pairing may include sequences: that comprise the same CDRs but with different framework regions, sequences that contain one or more mutations compared to the identified chain pairing, and sequences that contain one or more fragments of the identified chain pairing. Obtaining a candidate antigen-binding protein may comprise identifying a coding sequence for the candidate antigen-binding protein and expressing the sequence in a suitable expression system (such as e.g. in a suitable host cell).

The desired property may be a desired binding property (such as e.g. the ability to bind one or more targets, the ability to bind one or more targets with an affinity above one or more respective thresholds, etc.), a desired expression property (such as e.g. an increased expression level compared to a standard in one or more expression systems, an expression level above a predetermined level in one or more expression systems, a yield above a predetermined level in one or more expression systems, etc.), a desired stability property (such as e.g. a stability above a certain threshold in one or more conditions), or a combination thereof. The desired property may include the ability to bind a predetermined target. Testing the one or more candidate antigen-binding proteins for the desired property may comprise identifying one or more antigens that the one or more candidate antigen-binding proteins bind(s) to, for example by testing for binding to one or more candidate antigens. Testing the one or more candidate antigen-binding proteins for the desired property may comprise identifying one or more antigens that the one or more candidate antigen-binding proteins is/are likely to bind to, for example by comparison with one or more antibodies with known targets. The antigen-binding protein may be a therapeutic antibody, and the desired property may comprise binding of a therapeutic target. An antigen-binding protein may also be referred to herein as “immune protein”.

Testing the one or more candidate antigen-binding proteins for the desired property may comprise identifying the presence or absence of a desired phenotype in an organism (such as e.g. an animal model) or cell expressing the one or more candidate antigen-binding proteins. Identifying the presence of a desired phenotype may comprise expressing the one or more candidate antigen binding proteins in one or more model cells (e.g. one or more cell lines) or organisms (such as e.g. one or more animal models).

The method may further comprise optimising the sequence of at least one of the one or more candidate antigen-binding proteins. Optimising the sequence of a candidate antigen-binding protein may be performed for example using any antibody optimisation technique known in the art. Optimising the sequence of a candidate antigen-binding protein may be performed using information from the sequence data from which the chain pairing was identified, for example by analysing sequences similar to the input sequence from which the chain pairing was identified. Methods for optimising antigen-binding proteins are known in the art and include the methods described in Mason et al. [2021], Seeliger et al., [2015], Warszawski et al. [2019], Hsiao et al. [2019] and Richardson et al. [2021], amongst others. Any of these methods could be used within the context of the present invention.

The query sequence may comprise the heavy chain sequence (or part of the heavy chain sequence) of a known antibody. Thus, the first chain may be a heavy chain sequence or a part of a heavy chain sequence of a known antibody.

The query sequence may have been obtained by bulk BCR sequencing of the heavy chain repertoire in one or more samples. The method may comprise the step of obtaining the query sequence by bulk BCR sequencing of the heavy chain repertoire in one or more samples. The one or more samples may be from one or more subjects. The one or more subjects may have been identified as having a desired characteristic, such as e.g. a particular clinical phenotype or clinically relevant characteristic such as a biomarker profile. For example, the one or more subjects may be resilient to a particular disease or condition. The disease or condition may be selected from a cancer (such as e.g. breast cancer), a neurodegenerative disease (such as e.g. amyotrophic lateral sclerosis), and an infectious disease (such as e.g. COVID-19).

The method may comprise identifying a chain pairing (e.g. a heavy-light pairing) for a plurality of query chain sequences (e.g. heavy chain sequences) selected from the first (e.g. heavy) chain sequences identified in the one or more samples, thereby obtaining a set of chain pairings (e.g. heavy-light chain pairings).

The method may further comprise identifying one or more targets by screening antibodies from the same source(s) as the one or more samples against a plurality of candidate peptides. The plurality of candidate peptides may be selected based on the species from which the one or more samples originate. For example, the source of the one or more samples may be one or more human subjects and the antibody repertoire(s) from the same source(s) as the one or more samples may be screened against a set of candidate peptides representative of the human peptidome to select a plurality of candidate peptides.

Identifying an antigen that the one or more candidate antigen-binding proteins bind(s) to may comprise using one or more targets identified by screening antibodies from the same source(s) as the one or more samples against a plurality of candidate peptides. The method may further comprise filtering the set of identified chain pairings based on one or more criteria. The one or more criteria may apply to the identity of an antigen or set of antigens that a candidate antigen-binding protein bind(s) to or is predicted to bind to.

Providing one or more query sequences may comprise providing a first query (e.g. heavy) chain sequence and a second query (e.g. heavy) chain sequence, and identifying a corresponding (e.g. light) chain sequence for each of the one or more query sequences may comprise identifying one or more first corresponding (e.g. light) chain sequence(s) and one or more second corresponding (e.g. light) chain sequence(s). The method may further comprise comparing the first corresponding chain sequence(s) and the second corresponding chain sequence(s) to identify one or more light chains that may be suitable for use as the common corresponding (e.g. light) chain of a bispecific antibody that includes both of the first (e.g. heavy) chains.

According to a fourth aspect, there is provided a method of providing a tool for identifying an antigen-binding protein comprising a pair of chains, the method comprising: providing training data comprising training first and corresponding sequences from known first and corresponding chain pairs, and training a deep learning model to take as input a query first chain sequence and to produce as output at least one corresponding chain sequence, using the training data. The method of the present aspect may have any of the features described in relation to the first aspect. The method may have any one or more of the following features. The method may further comprise obtaining a vocabulary for encoding of the training first chain sequences and a vocabulary for encoding of the training corresponding chain sequences. The vocabulary may be obtained using an encoding scheme wherein any gene sequence identifier corresponds to an individual token. The vocabulary may be obtained using an encoding scheme wherein any sequence is encoded at least in part using tokens that each correspond to an individual amino acid. The vocabulary may be obtained using an encoding scheme wherein any sequence is encoded at least in part using tokens that each correspond to an individual k-mer or is encoded using byte-pair encoding.

Providing training data may comprise providing unpaired training first and corresponding chain sequences. The unpaired training first and corresponding chain sequences may be referred to as pre-training data. The method may further comprise training a first transformer based model using unpaired training first and/or corresponding (e.g. heavy and/or light) chain sequences and training a second transformer-based model using unpaired training corresponding and/or first (e.g. light and/or heavy) chain sequences, and using the pre-trained first and second transformer models to initialise the encoder and the decoder, respectively, of the deep learning model.

The first and second transformer based models may each comprise a BERT model or a variant thereof, such as e.g. BERT, RoBERTa, or DistilBERT, or an autoregressive transformer model, such as GPT-2. The first and second transformer based models may each comprise a RoBERTa model, a BERT model or a GPT-2 model.

The method may further comprise providing the trained deep learning model to a user.

The methods described herein are computer implemented unless context indicates otherwise, such as e.g. where a sample is obtained, processed, analysed, or a molecule or composition produced, tested or used for any other purpose.

According to a fifth aspect, there is provided a system comprising: a processor; and a computer readable medium comprising instructions that, when executed by the processor, cause the processor to perform the steps of the method of any embodiment of any preceding aspect. The instructions may case the processor to perform the steps of the method of any embodiment of the first and/or fourth aspects.

According to a sixth aspect, there is provided one or more computer readable media comprising instructions that, when executed by one or more processors, cause the one or more processors to perform the steps of the method of any embodiment of any preceding aspect. The instructions may case the processor to perform the steps of the method of any embodiment of the first and/or fourth aspects.

DETAILED DESCRIPTION OF THE INVENTION

In describing the present invention, the following terms will be employed, and are intended to be defined as indicated below.

Figure 4:
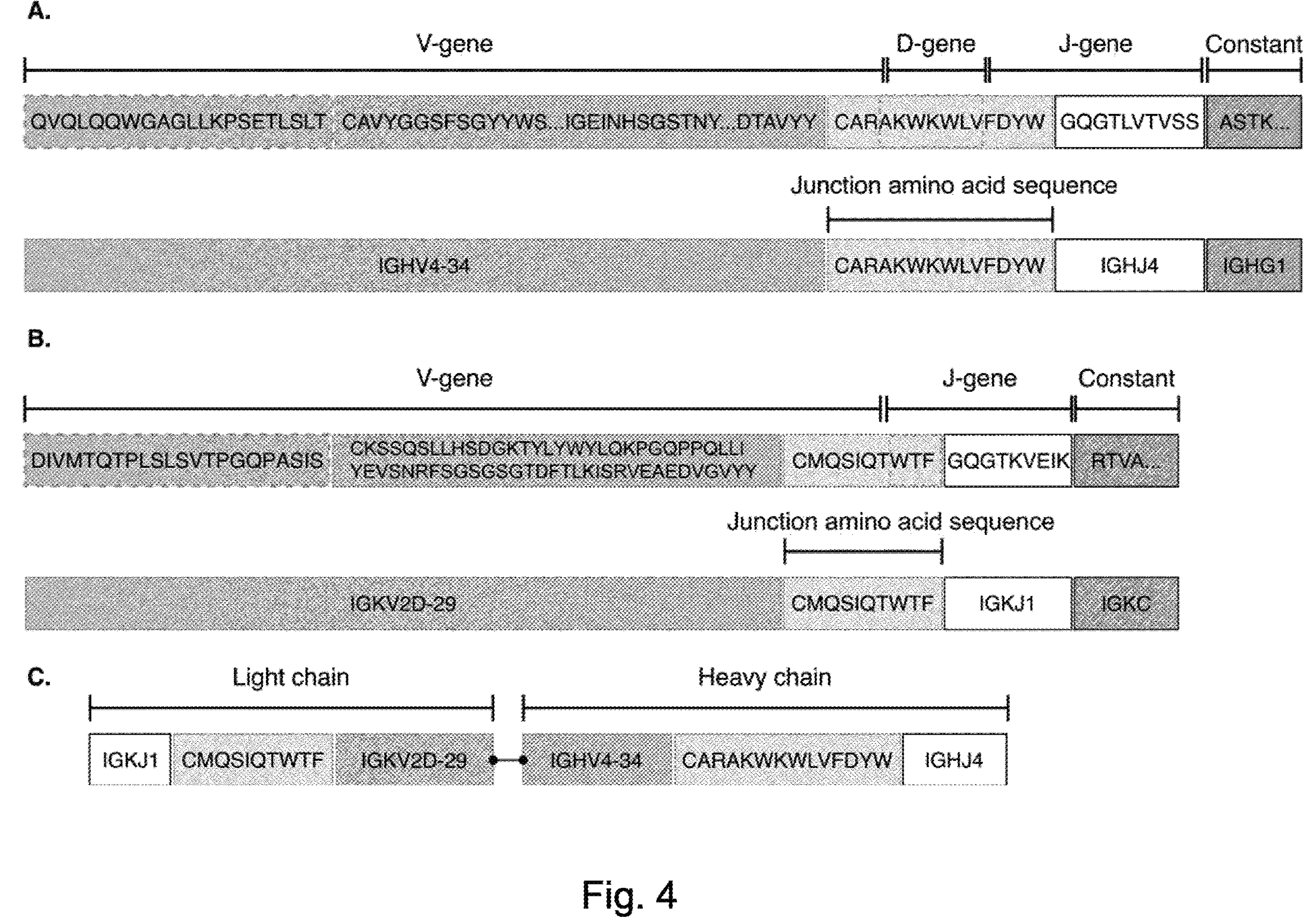
FIG. 4 illustrates schematically the architecture of a heavy chain and a light chain, as well as the configuration of data used herein in relation to this architecture. A. Architecture of an Ig heavy chain. The approximate boundaries of the V, D, and J genes are marked, along with the boundaries of the junction. A segment of the V-gene toward the N-terminus is in a dotted boundary as the read length from many NGS methods are too short to cover this region and/or some primers used for NGS are slightly inset within the V region. However, it is still possible to infer the V-gene using the sequence within the solid boundaries. B. Same as A., but for the light chain. C. A re-creation of the design of the paired read architecture from DeKosky et al. (2015).

A B cell receptor is a transmembrane protein expressed on the surface of B cells. A B cell receptor comprises a binding moiety (also referred to as "antigen-binding subunit" or "membrane immunoglobulin", "mIg") comprising a membrane bound immunoglobulin molecule (also referred to as antibody) that recognises a cognate antigen, and a signal transduction moiety. The membrane-bound immunoglobulin molecule comprises two immunoglobulin light chains and two immunoglobulin heavy chains, and is identical to a corresponding secreted antibody with the exception of an integral membrane domain. The signal transduction moiety is a heterodimer called Ig-α/Ig-β (CD79), bound together and to the immunoglobulin by disulfide bridges. An antibody (Ab) or immunoglobulin (Ig) is an immune protein, comprising an antigen binding site and a constant region belonging to one of a limited set of isotypes (IgA, IgD, IgE, IgG, or IgM) and mediating interactions with other components of the immune system. In humans and most mammals, antibodies comprise four polypeptide chains: two identical heavy chains and two identical light chains connected by disulfide bonds. Light chains typically consist of one variable domain $V_L$ and one constant domain $C_L$, while heavy chains typically contain one variable domain $V_H$ and three to four constant domains $C_H1$, $C_H2$, . . . . The variable domains form the antigen binding region and can also be referred to as the Fv region. Each variable domain contains three hypervariable regions referred to as the complementarity-determining regions (CDRs), which together form an antigen binding site. The variable region of each immunoglobulin heavy or light chain is encoded in several pieces-known as gene segments (subgenes): Ig heavy chains comprise variable (V), diversity (D) and joining (J) segments, and Ig light chains comprise V and J segments. Multiple copies of the V, D and J gene segments are present in the genome and developing B cells assemble an Ig variable region by (nearly) randomly selecting and combining one V, one D and one J gene segment (or one V and one J segment in the light chain), in a process called V(D)J recombination. The process involves the formation of double-stand breaks between the required segments, which form hairpin loops that are then joined together. The joining process is inaccurate, resulting in the variable addition or subtraction of nucleotides between the V and J (light chain) or V and DJ and D and J (heavy chain) segments, producing a large diversity in the sequences at the junction between segments (referred to as "junction sequences"). The V(D)J recombination process produces novel amino-acid sequences in the antigen-binding regions of Igs, generating a vast diversity of antigen recognition capability. As a result of the process, each Ig heavy chain variable region comprises: a V segment, a D segment and a J segment, with a junction sequence that spans the join between these segments (as illustrated on FIG. 4A). Similarly, each Ig light chain hypervariable region comprises: a V segment, and a J segment, and a junction sequence that spans the join between these segments (as illustrated on FIG. 4B). Within the variable region, CDR1 and CDR2 are found in the V segment, and CDR3 includes some of the V, all of D (in the heavy chain) and some of the J segment.

A T cell receptor is a membrane anchored protein expressed on the surface of T cells. A T cell receptor comprises a pair of protein chains that together form binding moiety that recognises a cognate antigen. These are expressed in a complex with constant T cell coreceptor chains CD3, comprising a CD3γ chain, a CD3δ chain, and two CD3ε chains in mammals. The constant chains associate with the T cell receptor and the constant ζ-chain to form the TCR complex, which together is able to generate a signal upon antigen binding to the T cell receptor. The TCR is a heterodimeric protein, comprising two highly variable chains, the α and β chains (in the majority of T cells), or the alternative γ and δ chains (in a minority of T cells). Each chain comprises two extracellular domains: a variable region (or variable domain) and a constant region (or constant domain, proximal to the cell membrane), a transmembrane region and a short cytoplasmic tail. The variable regions together bind to a peptide (antigen), within the context of a MHC (major histocompatibility complex) molecule in the case of as TCRs. Each variable domain contains three hypervariable regions referred to as the complementarity-determining regions (CDRs, respectively referred to as CDR1, CDR2 and CDR3 on each of the chains), which together form an antigen binding site. The TCR is a member of the immunoglobulin superfamily, which comprises BCRs and antibodies. In a process similar to that explained above, the variable region of each TCR chain is encoded in several pieces—known as gene segments (subgenes): β and δ chains comprise variable (V), diversity (D) and joining (J) segments, and α and γ chains comprise V and J segments. Multiple copies of the V, D and J gene segments are present in the genome and developing T cells assemble a TCR chain variable region by (nearly) randomly selecting and combining one V, one D and one J gene segment (or one V and one J segment in the α/γ chain), in a process called V(D)J recombination. The process involves the formation of double-stand breaks between the required segments, which form hairpin loops that are then joined together. The joining process is inaccurate, resulting in the variable addition or subtraction of nucleotides between the V and J (α/γ chain) or V and DJ and D and J (β/δ chain) segments, producing a large diversity in the sequences at the junction between segments (referred to as "junction sequences"). The V(D)J recombination process produces novel amino-acid sequences in the antigen-binding regions of TCRs, generating a vast diversity of antigen recognition capability. As a result of the process, each β/δ chain variable region comprises: a V segment, a D segment and a J segment, with a junction sequence that spans the join between these segments. Similarly, each α/γ chain hypervariable region comprises: a V segment, and a J segment, and a junction sequence that spans the join between these segments. Within the variable region, CDR1 and CDR2 are found in the V segment, and CDR3 includes some of the V, all of D (in the heavy chain) and some of the J segment.

As used herein, a "variable chain" (also referred to herein simply as "chain") of an antigen-binding protein refers to a chain of an antigen-binding protein that is involved in antigen recognition, or a part thereof that contains at least part of a variable region of the chain. Variable chains comprise variable regions that are responsible for the diverse repertoire of antigen recognition properties within antigen-binding proteins. A variable chain may be a BCR heavy or light chain, an antibody heavy or light chain, a TCR α or β chain, a TCR γ or δ chain, or any part of such chains that contains at least a part of one or more variable regions within these chains.

The B cell receptor repertoire (or corresponding antibody repertoire) present in a sample can be investigated using sequencing approaches. As explained above, two main sequencing approaches are used: single B cell sequencing, and sequencing of bulk B cell populations. As the BCR signalling moiety and antigen-binding moiety transmembrane domain is not variable, these techniques focus on the parts that are common between the B cell repertoire and the corresponding antibody repertoire. Thus, in the context of this disclosure, references to a BCR sequence, BCR repertoire, BCR heavy chain sequence, BCR light chain sequence, and any parts thereof, are used interchangeably with the corresponding antibody sequence, antibody repertoire, antibody heavy chain sequence, antibody light chain sequence, and corresponding parts thereof. For example, reference to sequencing a BCR heavy chain variable region equally is equivalent to sequencing the corresponding antibody heavy chain variable region, and the two terms may be used interchangeably. The term "antigen-binding protein" is used herein to refer to a BCR protein, a TCR protein, an antigen-binding moiety of a BCR protein, an antibody, or any parts thereof that maintain the antigen-binding property of the original BCR protein. TCR protein or antibody. Note that the repertoire of antibodies circulating in the blood of an individual may not match the B cell receptor repertoire present in the sample at the same time point. This is because antibodies that have been produced by B cells that are no longer present in the individual (e.g. because they have died) may be present in the sample. Thus, the term "corresponding antibody repertoire" refers to the repertoire of antibodies that would be expressed by the B cells present in a sample, not the repertoire of antibodies (proteins) that are actually present in the sample.

Single B cell sequencing can maintain the correspondence between heavy and light chain sequences. Two main approaches can be used to do this. The first approach is physical linkage of VH and VL [DeKosky et al., 2016]. The second approach is cell barcoding (such as e.g. provided by 10× Genomics) [King et al., 2021]. The physical linkage approach has a higher throughput than the cell barcoding approach, but it is more difficult to recover the full sequence. By contrast, cell barcoding has a lower throughput but allows easier recovery of the full sequence. No matter the approach, single B cell sequencing is limited in terms of throughput (to various extents), as explained above. Some single B cell sequencing technologies are additionally limited in terms of the length of the sequences recovered. As a result, BCR/antibody sequences identified using some single B cell sequencing methods may be limited to investigating a single CDR region, for example CDR3 (in other words, although the flanking V and J segments may be identified, they may not be fully sequenced to obtain the sequence of the CDR1 and CDR2 in the V segment), in both the heavy and light chain. In other words, datasets from single B cell sequencing methods may vary in the extent to which the sequence of the heavy and light chain is identified. Within the regions sequenced, it may also not be practical to sequence (or record) every single base of the V(D)J segments and as such sequencing efforts may focus on obtaining the junction sequence and enough information to identify the V, D and J genes. As a result, such methods may provide information comprising: the identity of the V, D and J segments (e.g. in the form of a V-/D-/J-gene segment identifier) for the heavy chain, the sequence of the junction segment in the heavy chain, the identity of the V and J segments (e.g. in the form of a V-/J-gene identifier) for the light chain, and the sequence of the junction segment in the light chain. The identity of the respective segments can be used to recover the corresponding germline sequence from a database. However, in cases where the data only contains the identity of the respective segments, any mutation that may be present in a particular chain (e.g. somatic mutations) compared to the reference germline sequence may not be captured. By contrast, sequencing of bulk B cell populations does not maintain the pairing between heavy and light chain sequences, but is less limited in terms of sequencing capabilities (in particular depth of sequencing of the BCR repertoire) within the heavy chain and light chain repertoires, respectively. Sequencing of bulk B cell populations may comprise sequencing of the heavy chain repertoire, the light chain repertoire, or both, of a B cell population. However, as mentioned above, due to the bulk nature of the process, even when both the light and heavy chain repertoires are sequenced, it is not possible to maintain the pairing information during the sequencing process. Such sequencing may produce information as sparse as that obtained with single cell B sequencing, or more detailed information including e.g. full CDR sequences, sequences of multiple CDRs, full variable region sequences, or full variable region sequences and enough of the constant region to determine the isotype of the sequence. Similar considerations apply to the sequencing of the T cell repertoire. In particular, many of the processes and limitations described above in relation to the study of B cell receptors and antibodies (and in particular in relation to the sequencing of these repertoires) apply to the T cell repertoire.

As used herein, the terms "variable chain sequence", encompasses the terms "heavy chain sequence", "light chain sequence", "α chain sequence", "β chain sequence", "γ chain sequence" and "δ chain sequence" and refer to any information that can be obtained from B cell sequencing or T cell sequencing technologies, ranging from a combination of one or more gene segment identifiers and/or junction sequences at one end, to full chain sequences at the other end. In particular, the terms "heavy chain sequence" and "light chain sequence" refer to any information that can be obtained from B cell sequencing technologies, ranging from a combination of one or more gene segment identifiers and/or junction sequences at one end, to full chain sequences at the other end. Further, the terms "variable chain sequence", "heavy chain sequence", "light chain sequence" "α chain sequence", "β chain sequence", "γ chain sequence" and "δ chain sequence" refer interchangeably to the amino acid sequence or the corresponding nucleic acid coding sequence. Similarly, a variable chain pairing or pair (such as heavy-light chain pairing or pair) refers to a combination of a heavy chain sequence and a light chain sequence, an α chain sequence and a β chain sequence, or a γ chain sequence and a δ chain sequence as defined herein, each ranging from a combination of one or more gene segment identifiers and/or junction sequences at one end, to full chain sequences at the other end.

Within the context of providing a desired antibody or antigen-binding protein, such as e.g. a therapeutic antibody, the term "antibody" (Ab) includes monoclonal antibodies, polyclonal antibodies, multispecific antibodies (e.g., bispecific antibodies), and antibody fragments that exhibit the desired biological activity and that comprise a heavy-light chain pairing identified as described herein or a heavy-light chain pairing derived from a heavy-light chain pairing identified as described herein (for example by further optimisation, affinity maturation, etc.).

A "sample" as used herein may be a cell or tissue sample, a biological fluid, an extract (e.g. a DNA or RNA extract obtained from the subject), from which B cell genomic material (e.g. RNA or DNA) can be obtained for genomic analysis, such as by sequencing (e.g. whole genome sequencing, whole exome sequencing, targeted/capture sequencing, RNA-seq, etc.). The sample may be a cell, tissue or biological fluid sample obtained from a subject (e.g. a biopsy). Such samples may be referred to as "subject samples". In particular, the sample may be a blood sample, a lymph node sample, a spleen sample, or a tumour sample, or a sample derived therefrom (such as e.g. by B cell purification, T cell purification, RNA extraction, etc.). As used herein, the terms "genomic material", "genomic sequencing" and the like encompasses both to the material/sequence present in the genome and the transcriptome of a sample, unless context indicates otherwise. The sample may be one which has been freshly obtained from a subject or may be one which has been processed and/or stored prior to genomic analysis (e.g. frozen, fixed or subjected to one or more purification, enrichment or extraction steps). The sample may be a cell or tissue culture sample. As such, a sample as described herein may refer to any type of sample comprising B cells or genomic material derived therefrom, whether from a biological sample obtained from a subject, or from a sample obtained from e.g. a cell line. The sample is preferably from a mammalian (such as e.g. a mammalian cell sample or a sample from a mammalian subject, such as a cat, dog, horse, donkey, sheep, pig, goat, cow, mouse, rat, rabbit or guinea pig), preferably from a human (such as e.g. a human cell sample or a sample from a human subject). Further, the sample may be transported and/or stored, and collection may take place at a location remote from the sequence data acquisition (e.g. sequencing) location, and/or any computer-implemented method steps described herein may take place at a location remote from the sample collection location and/or remote from the genomic data acquisition (e.g. sequencing) location (e.g. the computer-implemented method steps may be performed by means of a networked computer, such as by means of a "cloud" provider).

The term "sequence data" refers to information that is indicative of the presence of genomic material (DNA or RNA) or proteomic material in a sample that has a particular sequence. Thus, sequence data may comprise one or more nucleotide sequences and/or one or more amino acid sequences. Such information may be obtained using sequencing technologies, such as e.g. next generation sequencing (NGS), for example whole exome sequencing (WES), whole genome sequencing (WGS), whole transcriptome sequencing (RNAseq) or sequencing of captured genomic loci (targeted or panel sequencing). When NGS technologies are used, the sequence data may comprise a count of the number of sequencing reads that have a particular sequence. Sequence data may be mapped to a reference sequence, for example a reference genome, using methods known in the art (such as e.g. Bowtie (Langmead et al., 2009)). Thus, counts of sequencing reads or equivalent non-digital signals may be associated with a particular location or locus (where the "location" refers to a location in the reference genome or transcriptome to which the sequence data was mapped). Further, a location may contain a mutation, in which case counts of sequencing reads or equivalent non-digital signals may be associated with each of the possible variants (also referred to as "alleles") at the particular location. The process of identifying the presence of a mutation at a particular location in a sample is referred to as "variant calling" and can be performed using methods known in the art (such as e.g. general purpose NGS variant callers such as the GATK HaplotypeCaller, https://gatk-.broadinstitute.org/hc/en-us/articles/360037225632-HaplotypeCaller or tools specifically designed for immune sequences such as IgBLAST, https://www.ncbi.nlm.nih.gov/igblast/, [Ye et al., 2013]). Genomic sequence data may be converted to amino acid sequences by translating coding regions in silico (directly from an mRNA sequence or from identified coding regions in a genomic sequence), as known in the art.

As used herein "treatment" refers to reducing, alleviating or eliminating one or more symptoms of the disease which is being treated, relative to the symptoms prior to treatment. "Prevention" (or prophylaxis) refers to delaying or preventing the onset of the symptoms of the disease. Prevention may be absolute (such that no disease occurs) or may be effective only in some individuals or for a limited amount of time.

A composition as described herein may be a pharmaceutical composition which additionally comprises a pharmaceutically acceptable carrier, diluent or excipient. The pharmaceutical composition may optionally comprise one or more further pharmaceutically active polypeptides and/or compounds. Such a formulation may, for example, be in a form suitable for intravenous infusion.

As used herein, the terms "computer system" includes the hardware, software and data storage devices for embodying a system or carrying out a method according to the above described embodiments. For example, a computer system may comprise a central processing unit (CPU), graphical processing unit (GPU), input means, output means and data storage, which may be embodied as one or more connected computing devices. Preferably the computer system has a display or comprises a computing device that has a display to provide a visual output display (for example in the design of the business process). The data storage may comprise RAM, disk drives or other computer readable media. The computer system may include a plurality of computing devices connected by a network and able to communicate with each other over that network. It is explicitly envisaged that computer system may consist of or comprise a cloud computer. The term "processor" encompasses any processing unit or combination of processing units, including in particular CPUs and GPUs.

As used herein, the term "computer readable media" includes, without limitation, any non-transitory medium or media which can be read and accessed directly by a computer or computer system. The media can include, but are not limited to, magnetic storage media such as floppy discs, hard disc storage media and magnetic tape; optical storage media such as optical discs or CD-ROMs; electrical storage media such as memory, including RAM, ROM and flash memory; and hybrids and combinations of the above such as magnetic/optical storage media.

Identification Variable Chain Pairs

Figure 1:
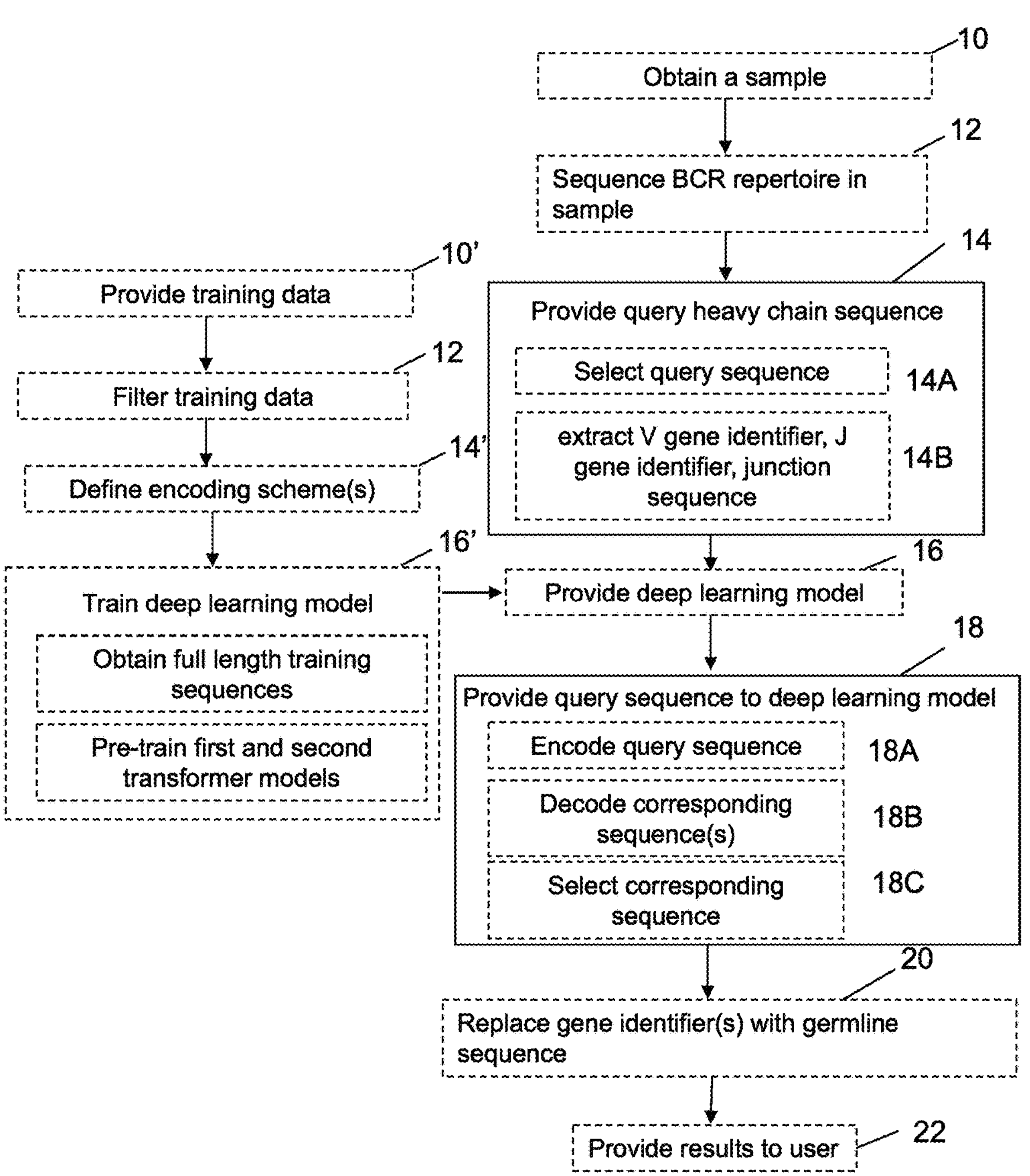
FIG. 1 is a flowchart illustrating schematically a method of identifying a chain pair according to the disclosure.

The present disclosure provides methods for identifying variable chain pairs from a variable chain sequence. An illustrative method will be described by reference to FIG. 1. FIG. 1 illustrates an embodiment in which a heavy or light chain sequence of a B cell receptor or antibody is used to identify heavy-light chain pairs. In other words, FIG. 1 illustrates an embodiment in which the variable chain sequences are BCR/antibody heavy and light chains from BCR. However, the method described by reference to FIG. 1 is applicable to embodiments in which a TCR $\alpha$, $\beta$, $\gamma$, or $\delta$ chain sequence is used to identify $\alpha\beta$ (if the input chain pair is an $\alpha$ or $\beta$ chain) or $\gamma\delta$ (if the input chain pair is a $\gamma$ or $\delta$ chain) chain pairs. At optional step 10, a sample comprising B cell genomic material (typically in the form of RNA, where the RNA encoding for the BCR expressed by the cells from which the B cell genomic material originated can be extracted and sequenced) may be obtained from a subject. Similarly, a sample comprising T cell genomic material may be used in embodiments where TCR chain pairs are identified. At step optional step 12, the BCR repertoire in the sample may be sequenced using bulk BCR sequencing. This may comprise sequencing the heavy chain BCR repertoire in the sample. Similarly, the TCR repertoire in the sample may be sequenced using bulk TCR sequencing. This may comprise sequencing the $\beta$ chain repertoire of in the sample. At step 14, a query chain sequence is provided. In the illustrated embodiment, the query sequence is a heavy chain sequence. In other embodiments, the query chain sequence may be a light chain sequence. Providing a query sequence may comprise selecting at step 14A a query sequence as one of the heavy chain sequences sequenced at step 12. Providing a query sequence may comprise providing at step 14B a sequence that comprises a V-gene sequence or identifier, a J-gene sequence or identifier, and a junction sequence. For example, step 14B may comprise extracting, from a bulk BCR sequencing data set, for a selected sequence, a V-gene sequence or identifier, a J-gene sequence or identifier, and a junction sequence. Similar steps may be performed in the context of TCR pairing, for example using a query $\beta$ chain sequence. At optional step 16, a deep learning model is provided, wherein the deep learning model is configured to take as input a query variable chain sequence and to produce as output at least one corresponding variable chain sequence. In the illustrated embodiment, the query sequence is a heavy chain sequence and thus the deep learning model is configured to take as input a query heavy chain sequence and to produce as output at least one corresponding light chain sequence. In other embodiments, the query chain sequence may be a light chain sequence and thus the deep learning model may be configured to take as input a query light chain sequence and to produce as output at least one corresponding heavy chain sequence. In yet other embodiments, the query chain sequence may be a β chain sequence (or an α, δ or γ chain sequence) and thus the deep learning model may be configured to take as input a query β chain sequence (or an α, δ or γ chain sequence) and to produce as output at least one corresponding α chain sequence (or at least one corresponding β, γ or δ chain sequence). The deep learning model may have been previously trained using training variable chain sequences from known variable chain pairs, such as training heavy and light chain sequences from known heavy-light chain pairs in the illustrated embodiment. Thus, providing a deep learning model may simply comprise retrieving a trained deep learning model from a computer-readable medium such as a memory associated with a processor executing the method, or otherwise receiving the trained deep learning model. The training of the deep learning model is explained in more detail below. Alternatively, the deep learning model may be trained as part of the present method, using training variable chain sequences from known heavy-light chain pairs, such as training heavy and light chain sequences from known heavy-light chain pairs in the illustrated embodiment.

At step 18, the query chain sequence is provided to the deep learning model. Step 18 may comprise optional step 18A of encoding the query sequence using a predetermined encoding scheme. Step 18 may comprise optional step 18B of decoding each of the corresponding sequences output by the deep learning model using a predetermined encoding scheme. The encoding scheme(s) used for the encoding and decoding schemes may have been previously defined based on the content of the training variable chain sequences (e.g. heavy and light) chain sequences used to train the deep learning model. Step 18 may comprise optional step 18C of selecting a sequence of the one or more corresponding variable chain sequences (a light chain sequence in the illustrated embodiment) that is associated with the highest confidence metric amongst the one or more corresponding variable chain sequences, where the deep learning model is configured to produce as output one or more corresponding chain sequences, each associated with a confidence metric such as a probability. Step 18C may be performed before or after step 18B. At optional step 20, one or more gene sequence identifiers in the at least one corresponding chain sequence (which is a light chain sequence in the illustrated embodiment) may be replaced with a corresponding germline sequence. At optional step 22, the results of any of the preceding steps (and in particular steps 18 and/or 20) may be provided to a user, for example through a user interface. These results may be used for example to provide a therapeutic antibody, as will be described further below. The method may be repeated for a plurality of query sequences. This may comprise repeating steps 14 to 18.

The training of the deep learning model will now be explained by reference to optional steps 10'-16'. At step 10', training data is provided comprising training variable chain sequences from known variable chain pairs. In the illustrated embodiment, the training data comprises heavy and light chain sequences from known heavy-light chain pairs. The training data may comprise at least 20,000 training chain pairs, at least 30,000, at least 40,000, at least 50,000, at least 60,000, at least 70,000, at least 80,000, at least 90,000, at least 100,000, at least 120,000 or at least 150,000 training chain pairs. In embodiments related to B cell receptors/antibodies, the training data may comprise at least 80,000, at least 100,000, at least 120,000 or at least 150,000 pairs of training heavy and light chain sequences. The training data may further comprise unpaired training sequences, which are heavy and light chain sequences in the illustrated embodiment. The unpaired training chain sequences may be referred to as "pre-training data". Thus, the training data may comprise training data per se (comprising paired chain sequences, in particular paired heavy and light chain sequences in the illustrated embodiment), and pre-training data (comprising unpaired chain sequences, in particular unpaired heavy and light chain sequences in the illustrated embodiment). The training data may comprise at least 100,000, at least 200,000, at least 300,000, at least 400,000, at least 500,000, at least 600,000, at least 700,000, at least 800,000, at least 900,000, at least 1 million (or at least 5, 10, 15, 20, 25, 30, 35 or 40 million) unpaired training chain sequences of the first type and/or of the corresponding type. The training data may comprise at least 1 million (or at least 5, 10, 15, 20, 25, 30, 35 or 40 million) unpaired training heavy chain sequences and at least 1 million (or at least 5, 10 or 15 million) unpaired training light chain sequences. As the skilled person understands, the amount of training and/or pretraining data may be limited by the amount of suitable data available, and may change as more data becomes available. Further, the amount of data available may depend on the particular use case, such as e.g. the identity of the first and corresponding chain sequences (e.g. more data may be available for αβ TCRs than for γδ TCRs which are rarer), the criteria used when filtering the data (see step 12') etc. The numbers provided may apply to the data prior to and/or after any filtering is applied. At step 12', the training data is filtered. For example, the training data may be filtered to exclude any pairs comprising a junction sequence (e.g. in the heavy and/or light chain) that is outside of a predetermined range of lengths. As another example, the training data may be filtered based on any feature of the data, including for example the cell type that the data was derived from, the organism, whether the data is from a naïve library, whether the data is from subjects that have been immunised with a particular antigen, etc. In other words, the training data may be filtered to ensure that the training data only contains (inclusion filter) or does not contain (exclusion filter) data with one or more features of interest. At step 14', one or more encoding schemes are defined for the training data by obtaining a vocabulary for encoding of the training chain sequences, in particular for encoding of the training heavy chain sequences and a vocabulary for encoding of the training light chain sequences in the illustrated embodiment. Defining an encoding scheme may comprise excluding from the vocabulary constructed based on the content of the training chain sequences any token that is used a number of times below a predetermined threshold (e.g. 2) in the training data. At step 16', the training data is used to train a deep learning model to take as input a query heavy chain sequence (in the illustrated embodiment) and to produce as output at least one corresponding light chain sequence (in the illustrated embodiment), using the training data. Training the deep learning model may comprise first training a transformer-based model using the unpaired training chain sequences, and using the pre-trained transformer model to initialise the encoder and the decoder, of the deep learning model. Alternatively, training the deep learning model may comprise training a first and second transformer-based model using the unpaired training chain sequences of the first type and of the second type, respectively (the first type being the heavy chain and the second type being the light chain, in the illustrated embodiment), and using the pre-trained transformer model to initialise the encoder and the decoder, respectively, of the deep learning model. Training the deep learning model may comprise obtaining training sequences that comprise full length sequences for the variable region of the second type of chain and/or the first type of chain (e.g. the light chain and/or the heavy chain, in the illustrated embodiment) by imputing missing sequence information, if the chain sequences from known chain pairs do not comprise full length sequences for said variable regions.

Systems

Figure 2:
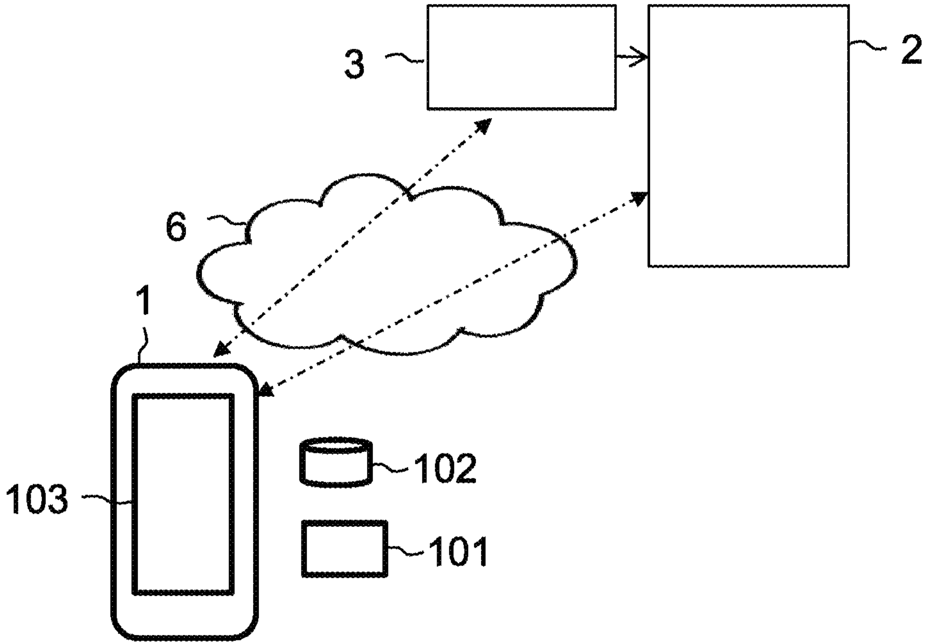
FIG. 2 shows an embodiment of a system for identifying a chain pair according to the disclosure.

FIG. 2 shows an embodiment of a system for identifying a variable chain pair from an input variable chain, according to the present disclosure. The system comprises a computing device 1, which comprises a processor 101 and computer readable memory 102. In the embodiment shown, the computing device 1 also comprises a user interface 103, which is illustrated as a screen but may include any other means of conveying information to a user such as e.g. through audible or visual signals. The computing device 1 is communicably connected, such as e.g. through a network 6, to sequence data acquisition means 3, such as a sequencing machine, and/or to one or more databases 2 storing sequence data. The one or more databases may additionally store other types of information that may be used by the computing device 1, such as e.g. reference sequences, parameters, etc. The computing device may be a smartphone, server, tablet, personal computer or other computing device. The computing device is configured to implement a method for identifying a variable chain pair from an input variable chain (suitably a heavy chain or a β chain, preferably a heavy chain), as described herein. In alternative embodiments, the computing device 1 is configured to communicate with a remote computing device (not shown), which is itself configured to implement a method of identifying a variable chain pair from an input variable chain, as described herein. In such cases, the remote computing device may also be configured to send the result of the method to the computing device. Communication between the computing device 1 and the remote computing device may be through a wired or wireless connection, and may occur over a local or public network such as e.g. over the public internet or over WiFi. The sequence data acquisition 3 means may be in wired connection with the computing device 1, or may be able to communicate through a wireless connection, such as e.g. through a network 6, as illustrated. The connection between the computing device 1 and the sequence data acquisition means 3 may be direct or indirect (such as e.g. through a remote computer). The sequence data acquisition means 3 are configured to acquire sequence data from nucleic acid samples, for example genomic DNA samples or RNA samples extracted from B cells or T cells purified from fluid and/or tissue samples (such as e.g. peripheral blood, spleen, lymph node, tumour tissue, or any other type of sample comprising B cells or T cells). In some embodiments, the sample may have been subject to one or more preprocessing steps such as DNA/RNA purification, fragmentation, library preparation, target sequence capture (such as e.g. exon capture and/or panel sequence capture). Any sample preparation process that is suitable for use in the determination of a B cell receptor sequence or repertoire may be used within the context of the present invention. The sequence data acquisition means is preferably a next generation sequencer. The sequence data acquisition means 3 may be in direct or indirect connection with one or more databases 2, on which sequence data (raw or partially processed) may be stored.

Applications

The above methods find applications in any context where it is desirable to identify an antibody or BCR that is likely to bind its target from information that is limited to the heavy chain, the light chain or parts thereof (such as e.g. the V-gene, J-gene and junction sequences). This is frequently the case in the context of the discovery process of antibody therapeutics. Antibody therapeutics have been shown to be successful approaches for a wide range of diseases from neurodegenerative diseases to cancer. Thus, the approaches described herein find use in the context of providing therapeutics in each of these clinical contexts. Further, the methods described herein can be used to identify a potentially functional antibody or BCR from any input heavy/light chain or part thereof, whether the input information is newly generated for a particular purpose (e.g. from patients or samples identified as having a desired phenotype) or from existing/historical data sets (for example to mine or re-mine existing datasets to discover new therapies or identify immune proteins that could explain why certain clinical phenotypes persist).

Thus, the invention also provides a method of providing an antibody therapeutic, the method comprising identifying a heavy-light chain pairing using any of the methods described herein, or that is derived from a heavy-light chain pairing that has been identified using any of the methods described herein (such as e.g. by further optimisation, mutation, etc). The heavy-light chain pairing may be obtained for an input heavy chain sequence that has been obtained by bulk BCR sequencing of the heavy chain repertoire in one or more samples. The one or more samples may be from one or more subjects. The one or more subjects may have been identified as having a desired characteristic, such as e.g. a particular clinical phenotype or clinically relevant characteristic such as a biomarker profile. For example, the one or more subjects may be resilient to a particular disease or condition. The disease or condition may be selected from a cancer (such as e.g. breast cancer), a neurodegenerative disease (such as e.g. amyotrophic lateral sclerosis), or an infectious disease (such as e.g. COVID-19). The method may comprise identifying a heavy-light chain pairing for a plurality of input heavy chain sequences selected from the heavy chain sequences identified in the one or more samples, thereby obtaining a set of heavy-light chain pairings. The method may further comprise identifying the target (or a putative target or sets of targets) of the heavy-light chain pairing or each heavy-light chain pairing in the set of heavy-light chain pairings. The method may further comprise identifying one or more targets by screening antibodies from the same source(s) as the one or more samples against a plurality of candidate peptides. The plurality of candidate peptides may be selected based on the species from which the one or more samples originate. For example, the source of the one or more samples may be one or more human subjects and the antibody repertoire(s) from the same source (s) as the one or more samples may be screened against a set of candidate peptides representative of the human peptidome. Identifying the target (or a putative target or sets of targets) of the heavy-light chain pairing or each heavy-light chain pairing in the set of heavy-light chain pairings may comprise using one or more targets identified by screening antibodies from the same source(s) as the one or more samples against a plurality of candidate peptides. The method may further comprise filtering the set of heavy-light chain pairings based on one or more criteria. The one or more criteria may apply to the identity of the putative targets or sets of targets identified for a heavy-light chain pairing.

The method may further comprise obtaining an antibody or fragment thereof which comprises an identified heavy-light chain pairing or a heavy-light chain pairing derived from an identified heavy-light chain pairing. Obtaining an antibody or fragment thereof may comprise identifying a coding sequence for the antibody or fragment thereof and expressing the sequence in a suitable expression system (such as e.g. in a suitable host cell). The method may further comprise identifying one or more antigens that the antibody or fragment thereof binds to, for example by testing for binding to one or more candidate antigens. The method may further comprise optimising the sequence of the antibody or fragment thereof. Optimising the sequence of the antibody or fragment thereof may be performed using any antibody optimisation technique known in the art. Optimising the sequence of the antibody or fragment thereof may be performed using information from the sequence data from which the heavy-light chain pairing was identified, for example by analysing sequences similar to the input sequence from which the heavy-light chain pairing was identified.

The invention also provides a method for providing an immunotherapeutic composition, the method comprising identifying a heavy-light chain pairing as described herein and producing an immunotherapeutic composition that comprises an antibody comprising the heavy-light chain pairing or an antibody that has been derived from the heavy-light chain pairing (such as e.g. by further optimisation, mutation, etc).

The methods described herein may also find uses in the context of providing bispecific antibodies. For example, the methods described herein may be used to identify a light chain that would be suitable for pairing with two different heavy chains of interest. Thus, the invention also provides a method of providing a bispecific antibody, the method comprising identifying a common light chain pairing for each of two heavy chains using any of the methods described herein, or a combination of a common light chain and two heavy chains that is derived from a heavy-light chain pairing that has been identified using any of the methods described herein (such as e.g. by further optimisation, mutation, etc). In such embodiments, it may be advantageous for the deep learning model to output a plurality of corresponding light or heavy chain sequence. For example, the deep learning model may be used to predict a first plurality of corresponding light chain sequences for a first heavy chain sequence and to predict a second plurality of corresponding light chain sequences for a second heavy chain sequence. The first and second plurality of light chain sequences predicted may then be compared to identify one or more light chains that may be suitable for use as the common light chain of a bispecific antibody that includes both of the heavy chains.

The methods described herein may also find uses in the context of antibody optimisation. For example, the methods described herein may be used to identify a light chain that would be suitable for pairing with a heavy chain, where the paring has one or more advantageous properties (such as e.g. improved functional or developability properties) compared to an original pairing for the heavy chain. Thus, the invention also provides a method of providing an improved antibody, the method comprising identifying a heavy-light chain pairing using any of the methods described herein from an input heavy chain of an original antibody, or a heavy-light chain pairing that is derived from a heavy-light chain pairing that has been identified using any of the methods described herein (such as e.g. by further optimisation, mutation, etc). The methods described herein also find applications in any context where it is desirable to identify a TCR that is likely to bind its target from information that is limited to the β chain, the α chain (or, in less common cases, the γ or δ chain) or parts thereof (such as e.g. the V-gene, J-gene and junction sequences). This is frequently the case in the context of the discovery process of cell therapeutics such as engineered T cells. Thus, the invention also provides a method of providing a TCR-based therapeutic, such as an engineered T cell expressing a particular TCR, the method comprising identifying an αβ or γδ chain pairing using any of the methods described herein, or that is derived from an αβ or γδ chain pairing that has been identified using any of the methods described herein (such as e.g. by further optimisation, mutation, etc). Thus, the methods described herein may also find uses in the context of T cell receptor optimisation, in a similar way as described above for antibodies.

The following is presented by way of example and is not to be construed as a limitation to the scope of the claims.

EXAMPLES

These examples describe a method of identifying heavy-light chain pairings according to the present invention, and validate it using single-cell datasets with known pairings as well as newly acquired experimental data.

Methods

Datasets

Summary statistics of all datasets are described in Table 1 below. We describe the sources and stratification of training, validation, test, and blind test sets below.

TABLE 1

Summary of datasets described in the work.

| Dataset | Methodology | Donors | # unique heavy-light pairs | Reference |
|---|---|---|---|---|
| Training | Single-cell emulsion | 6 | 153889 | DeKosky et al., 2015; DeKosky et al., 2016 |
| Validation | Single-cell emulsion | 6 | 17099 | DeKosky et al., 2015; DeKosky et al., 2016 |
| Test | Single-cell emulsion | 6 | 18999 | DeKosky et al., 2015; DeKosky et al., 2016 |
| Eccles | 10x single-cell | 1 | 741 | Eccles et al., 2020 |
| King | 10x single-cell | 7 | 30332 | King et al., 2021 |
| Setliff | 10x single-cell | 2 | 4944 | Setliff et al., 2019 |

Training, validation and test sets: Paired heavy-light chain sequences were combined from three donors in DeKosky et al., [2015], and three naïve BCR libraries from DeKosky et al.

These datasets contain entries each comprising: the heavy chain V gene identifier, heavy chain junction sequence (nucleotide and amino acid), heavy chain J gene identifier, light chain V gene identifier, light chain junction sequence (nucleotide and amino acid), and light chain J gene identifier. This training set was picked primarily due to public availability and size. Note that the data entries also comprised the heavy chain D gene identifier but this information was not used. This is because annotation of D genes is believed to be less accurate than annotation of V and J genes. Sequences were filtered to those with heavy chain junctions between 7-30 amino acids in length and light chain junctions between 7-20 amino acids in length. This is because sequences with junction sequences outside of these boundaries are believed to be rare and increasing lengths come at a cost in terms of computing power that would be unlikely to be balanced by the gain in information to longer sequences being rare. This filter removed 84 pairs that had a heavy chain junction with a size outside of the boundaries, and 168 pairs that had a light chain junction with a size outside of the boundaries. The data was also filtered for sequences where the heavy chain V-gene and light chain V-gene were observed in at least two sequences in order to keep a more concise vocabulary. Indeed, an increased vocabulary size comes at a cost of additional model parameters to train, which is unlikely to be balanced by benefits in including very rare V-genes. This filter only removed a small number of entries. Indeed, only one heavy chain V-gene amongst the starting pairs was observed once. All of the light chains were observed in at least 2 sequences. Sequences with IMGT pseudogenes (entries comprising a sequence labelled as pseudogene in the Immunogenetics database, http://www.imgt.org, which are sequences whose coding region has stop codon(s) and/or frameshift mutation(s), and/or a mutation that affects the initiation codon) were also removed. Finally, any duplicate heavy-light chain pairs were removed, which is functionally equivalent to a 99% redundancy cut-off (in other words, any heavy-light chain pair across the different sets would be at most 99% identical, confirming that the pairs in the training data set are indeed unique). The length and number of entries filters together removed a total of 253 pairs (84+168+1) out of the 190,240 starting pairs that passed the pseudogene and redundancy filters, leading to a remaining set of 189,987 pairs (see Table 1).

The 189987 sequences were split into training, validation, and test sets of 153889, 17099, and 18999 sequences (corresponding to an ~80% training/10% validation/10% test split). While the same heavy chain sequence can be present across the three sets, none of these heavy chains have an identical light chain partner.

Training data investigation: the features of the training data were investigated using a $\chi^2$ test on heavy-light chain pairs with at least 5 observations in the training set. This showed that heavy-light chain pairing was not random ($\chi^2$=8102.9, p-value<$10^{-9}$). However, heavy-light chain pair contingency tables are not consistent between studies, making inferences regarding the randomness of pairing inconclusive. At the sequence level, a single heavy chain sequence typically had one unique partner light chain sequence, though there can be up to 7 different light chain partners per heavy chain. Light chains were found to be more promiscuous, where a single light chain sequence was found to pair with up to 1042 different heavy chains. Nevertheless, 58123 out of 73549 light chains had one unique heavy chain partner.

Blind test sets: single-cell datasets were obtained from the paired Observed Antibody Space [Kovaltsuk et al., 2018]. Three studies of human BCR repertoires from King et al., [2021], Eccles et al., [2020], and Setliff et al., [2019] were collected. In total, there were 30332, 741, and 4944 unique heavy-light chain pairs, respectively.

Sequence Tokenisation

The training set data did not contain full-length heavy chain and light chain sequences, because the single-cell sequencing method used to generate this data was not able to recover the full amino acid sequence of the light/heavy chain. Instead, the training data set contained: (i) for each heavy chain: the V gene identifier, the junction sequence the J gene identifier, and the D gene identifier (although the latter was not used), and (ii) for each light chain: the V gene identifier, the junction sequence, and the J gene identifier. Thus, each entry comprised a combination of gene identifiers and sequences such as e.g. IGHV3-23/CAR . . . DYW/IGHJ6-IGKV3-20/CQQ . . . /IGKJ2. The models were trained to take as input a tokenised heavy chain sequence corresponding to a V gene identifier, a junction sequence and a J gene identifier, and to produce as output a tokenised light chain sequence corresponding to a V gene identifier, a junction sequence and a J gene identifier. In order to deal with this data format, a custom encoding method was designed for their tokenisation. Each V-gene constituted a single token, each J-gene, constituted a single token, and the junction amino acid sequence was tokenised as overlapping 3-mers. The junction sequence is the most diverse region of the sequence, and is believed to mediate most of the binding functionality, hence the increased granularity in tokenisation of this sequence. Tokens were used if there was a minimum of 2 occurrences in the training set (as already explained above in relation to filtering of the data).

Other possible schemes for the tokenisation of the junction amino acid sequences (or the full sequence) include for example byte-pair encoding, or tokens for each amino acid. Schemes such as byte-pair encoding may be particularly useful if more full-sequence sequence data was available, such as e.g. if single-cell data in the order of hundreds of thousands, or even millions of sequences, was used for training the model.

In total, 7986 tokens were constructed in the heavy chain vocabulary, while the light chain vocabulary had 6452 tokens. In the context of this example, a "sentence" is a tokenised representation of a heavy or light chain sequence. Each sentence starts with the special token <SOS>, followed by a token representing the heavy or light chain's V-gene, the overlapping 3-mer tokens, the J-gene token, and then the special token <EOS>. For any sentence with fewer tokens than the maximum length of 34 and 24 for the heavy and light chains respectively, the sequence was padded with the special <PAD> token. If a sequence contains an unobserved V-gene, J-gene, a novel 3-mer, or the junction is longer than 30 amino acids, Matchmaker does not make a prediction. In practice, the J-gene diversity is significantly lower than the V-gene diversity and therefore there were no instances of unobserved J-genes.

Light Chain Pairing Methods

Five strategies for light chain prediction using only the heavy chain as input were investigated. These are illustrated on FIG. 3 and further detailed below. They include:

- A transformer architecture with heavy chain tokenisation and light chain token conversion to sequence (referred to as "Matchmaker" in FIG. 3A and below);
- a GRU (gated recurrent unit) model with heavy chain input using the same vocabulary as for the transformer, and also providing a light chain output (FIG. 3B); GRUs, and more broadly, other recurrent neural network (RNN) architectures such as LSTMs (long short term memory networks) with attention were the previous "state of the art" for neural machine translation before transformers became common for this task;
- a database search method workflow (FIG. 3C);
- a variation of the database search method termed "random search"; and
- a frequency searching method that matches the ranked distributions of heavy and light chain read counts, then pairs similarly ranked chains (FIG. 3D).

Four of these methods (transformer. GRU, database search, random search) were newly developed as part of this work. The frequency searching approach is based on the approach previously described in Reddy et al., 2010.

Matchmaker architecture and inference: Matchmaker was built with PyTorch (version 1.6.0). Matchmaker's hyperparameters and optimisation procedure is similar to the sequence-to-sequence (Seq2Seq) transformer from Vaswani et al. [2017]. Deviations from the original Transformer of Vaswani et al. [2017] are described below. In summary, the model was made slightly smaller (fewer layers) for better constraining, and was trained using a different optimisation technique to improve training. Matchmaker has 4 encoder layers and 4 decoder layers, with a feed-forward dimension of 1024, and a dropout of 0.2. Layer normalisation was applied within the residual block [Child et al., 2018; Xiong et al., 2020]. The model was optimised using AdamW, with a weight decay of 0.1. Gradient clipping was implemented with a L2 norm of 1.0. Matchmaker has a total of 31.7M learnable parameters. Training was stopped if the validation loss did not improve for 3 epochs, and the model with the best validation loss was used.

Gated recurrent unit (GRU) neural network model: An alternate deep learning Seq2Seq model with an attention mechanism [Bahdanau et al., 2015] was trained using two GRU networks [Cho et al., 2014]. Here, the encoder is a 4-layer bi-directional GRU with a hidden dimension of 1024, and the decoder is a 4-layer, forward-only GRU with a hidden dimension of 1024. Other hyperparameters of the model, such as the dimension of the embedding layers, were matched as close to Matchmaker as possible. In total, this model has 131.8M learnable parameters. The encoder-decoder GRU model was trained in an identical manner to Matchmaker. For simplicity, this architecture is referred to as the "GRU model".

GRU networks (and by extension, recurrent neural networks) have an entirely different mechanism of how they process sequences compared to Transformers. Briefly, transformers use a series of "self-attention" mechanisms that make them not only faster, but more accurate, while recurrent nets do not have this at all.

Both the Matchmaker model and the GRU model as used in this study provided a single prediction for each input chain. In particular, the models predicted each chain in a sequential manner, by: at each subsequent position, outputting a probability for all possible tokens for the current position, and selecting the token with the highest probability for the current position before moving on to the next position. Other implementations are possible and envisaged. For example, a plurality of tokens could be considered simultaneously at each position and a combination of tokens across a plurality of positions (such as e.g. the whole sequence, i.e. all positions) that optimise a global probability across the plurality of positions can be selected. This may be performed using a beam search approach, or a related approach such as beam stack search [Zhou & Hansen, 2005] and depth-first beam search [Furcy & Koenig, 2005]. Beam search is a heuristic search algorithm that explores a graph by expanding the most promising node in a limited set. After having reached a predetermined maximum depth, a solution with maximum probability may be output. Database search method: Heavy chains were paired by sequence homology to known heavy-light chain pairs in Matchmaker's training set. For a query heavy chain sequence, only heavy-light chain pairs with a matching heavy chain V-gene to the query are selected. From this subset, two pairs are selected. The first is the "closest" light chain, which is from the pair with the closest heavy chain junction amino acid sequence to the query. The second is the "top" light chain, which is from the pair with the light chain V-gene that is most often associated with the query heavy chain's V-gene. The closest light chain is used if the identity to the query junction amino acid sequence is ≥65%, or the germline V-gene identities between the closest and top light chains are ≥75%. Otherwise, the top light chain is used. The rationale to distinguish these two cases is that if there is a sufficiently similar junction sequence in the search, then the VL sequence from this could be used. If there is not one sufficiently similar, then a more coarse approach is taken where the most common VL for that V gene is used. Different cutoffs or even no cutoff (i.e. using the closest light chain in all cases) could be used. For either case, this strategy is referred to as the "database search" method.

Random search method: with this approach, one light chain is chosen randomly from the database without any regard to features of the heavy chain.

Frequency-based search method: As a baseline, a search for light chain pairs was performed using read counts. Since all the datasets used in this study are pre-paired, a situation with two bulk sequencing libraries was emulated by first disassembling the paired sequences. The number of reads was then aggregated onto the heavy chain sequence, or the light chain sequence. For example, suppose there are sequences HeavyA:LightA with 4 reads and HeavyB:LightA with 5 reads; splitting and aggregation results in HeavyA with 4 reads, HeavyB with 5 reads, and LightA with 9 reads. Heavy chains and light chains are then ranked on the basis of their total read count (see FIG. 3D). Heavy chains are then paired with light chains with matching ranks.

Figure 3:
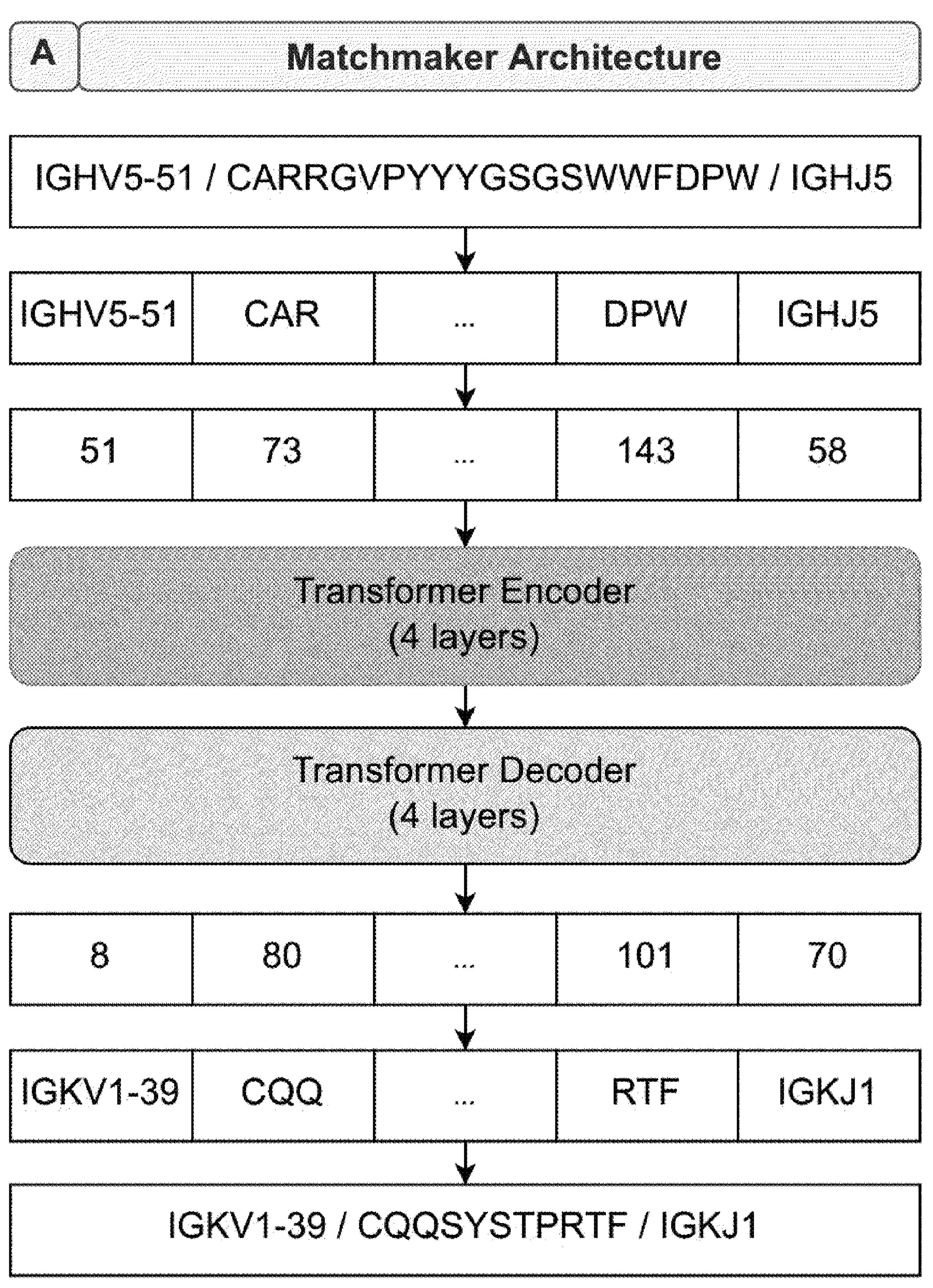
FIG. 3 illustrates schematically a plurality of methods for light chain prediction using only the heavy chain as input. A: Transformer architecture with heavy chain tokenisation and light chain token conversion to sequence. B: GRU model with heavy chain input and light chain output. C: database search method workflow. D: Frequency searching matches the ranked distributions of heavy and light chain read counts, then pairs similarly ranked chains. Random search is a variation of the database search method and is not illustrated.
Figure 3:
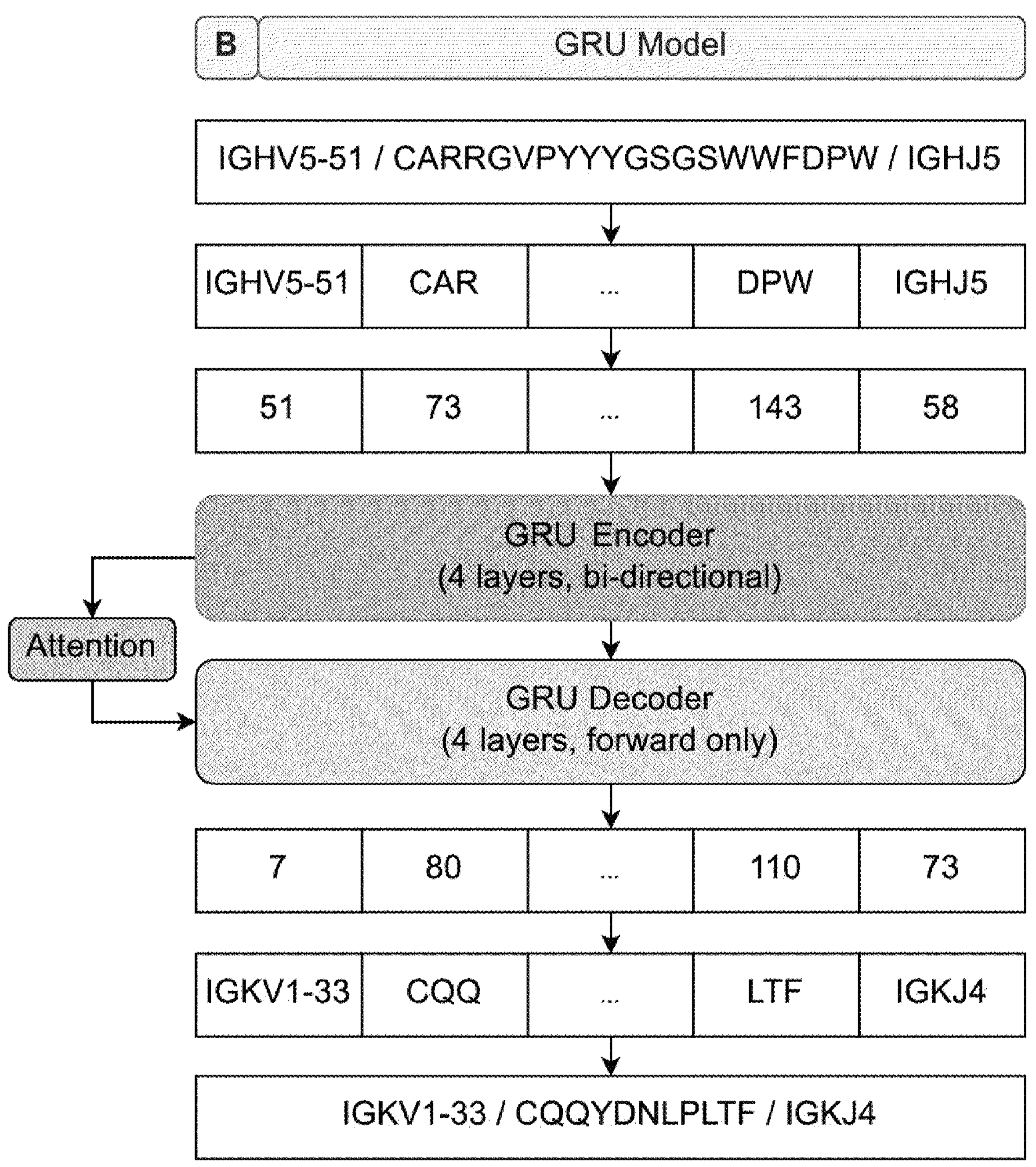
Figure 3:
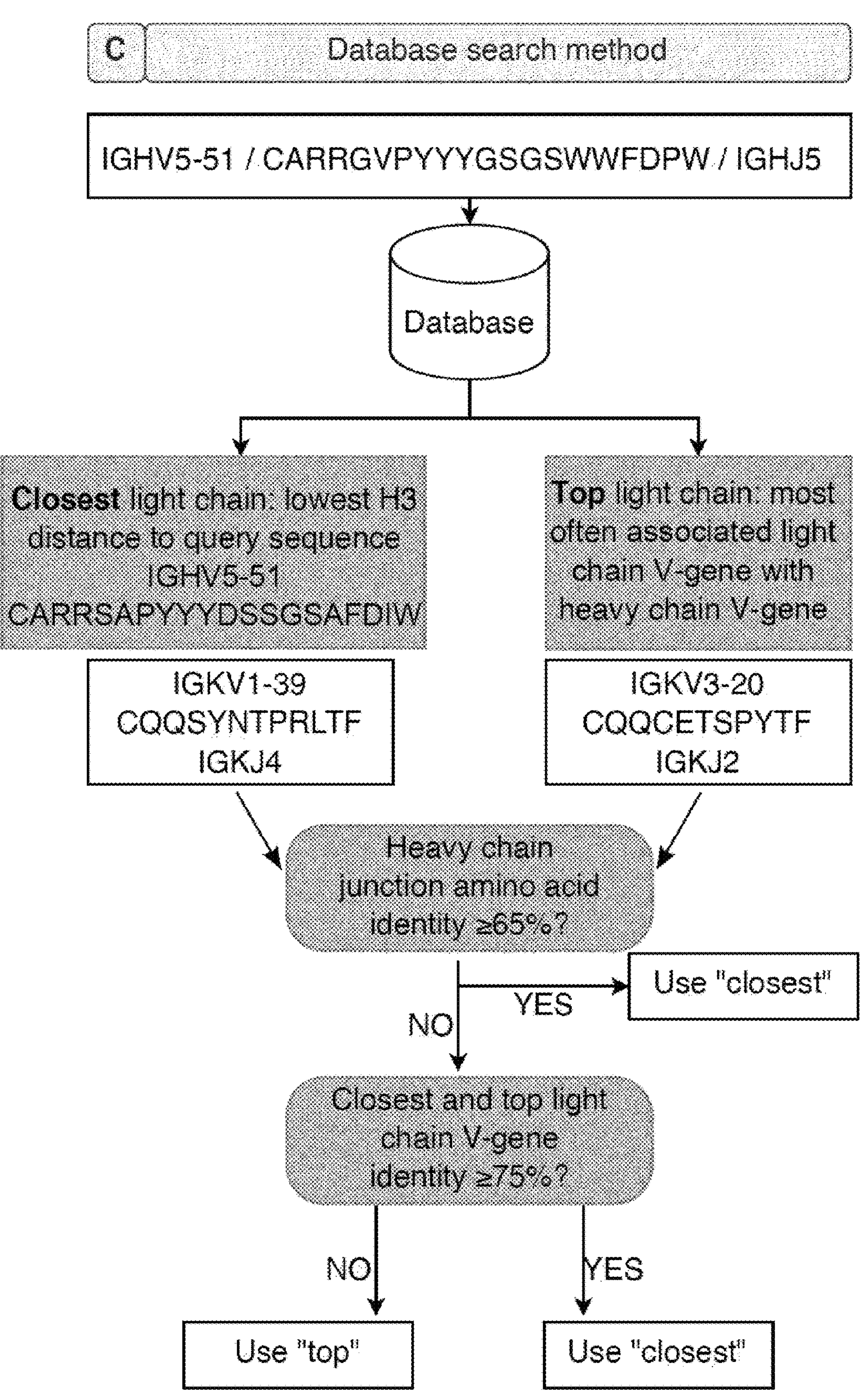
Figure 3:
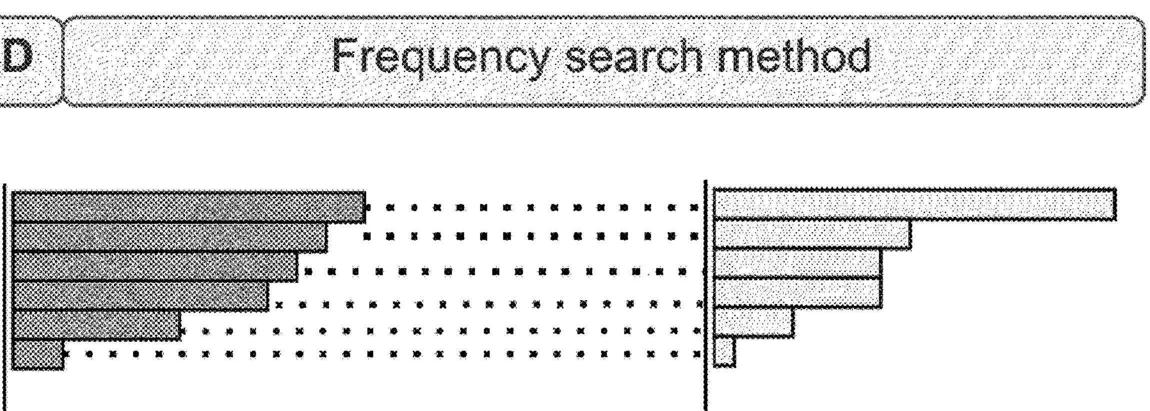

Construction of full light chain sequences: for all methods described above, the output is a light chain V-gene identifier, junction amino acid sequence, and the light chain J-gene identifier (FIG. 3). Since the training set does not have full-length sequences, the light chain V-gene and J-genes were replaced with their germline amino acid sequences.

Characterisation of Monoclonal Antibodies Binding to their Cognate Target Antigens The computationally paired versions of each therapeutic antibody were characterised for binding to their respective cognate antigen by an indirect ELISA. Briefly, commercially sourced recombinant versions of the antigens (see Table 2 below) were immobilised, and antibodies applied in solution as a 10-point titration using a top concentration of 500 nM and a 3-fold dilution series. Anti-human IgG secondary antibody conjugated to HRP (horseradish peroxidase) was used to detect antibodies still bound after washing. Absorbances at 450 nm were read after developing with TMB-ELISA substrate and stopping with sulfuric acid. Absorbances were then plotted against concentration using GraphPad Prism 9 (www.graphpad.com).

TABLE 2

Commercially sourced antigens used for ELISA

| Antigen | Construct | Catalogue No. |
|---|---|---|
| Recombinant Human ErbB2/Her2 Fc Chimera with C-term His tag | Thr23-Thr652 Acc# NP_004439 | 1129-ER |
| Recombinant Human PD-L1/B7-H1 Fc Chimera | Ph19-Thr239 Acc# Q9NZQ7 | 156-B7 |
| Recombinant Human PD-1 Fc Chimera | Leu 25-Gln167 Acc# Q15116 | 1086-PD |
| Recombinant Human EGFR Fc Chimera | Leu25-Ser645 Acc#CAA25240 | 344-ER |
| Recombinant Human Siglec-3/CD33 Fc Chimera Protein | Asp18-His259 Acc# AAA51948 | 1137-SL |

Thermostability of Monoclonal Antibodies

Thermostability of the monoclonal antibodies was measured in a thermal denaturation assay. In triplicate, each antibody was heated from 25° C. to 95° C. in the presence of SYPRO™ orange, and the fluorescence measured. The melt curve derivatives were then plotted as the average of the three replicates. The temperature at which the fluorescence was most rapidly increasing was noted for each antibody.

Tandem Transformer Model

Figure 9:
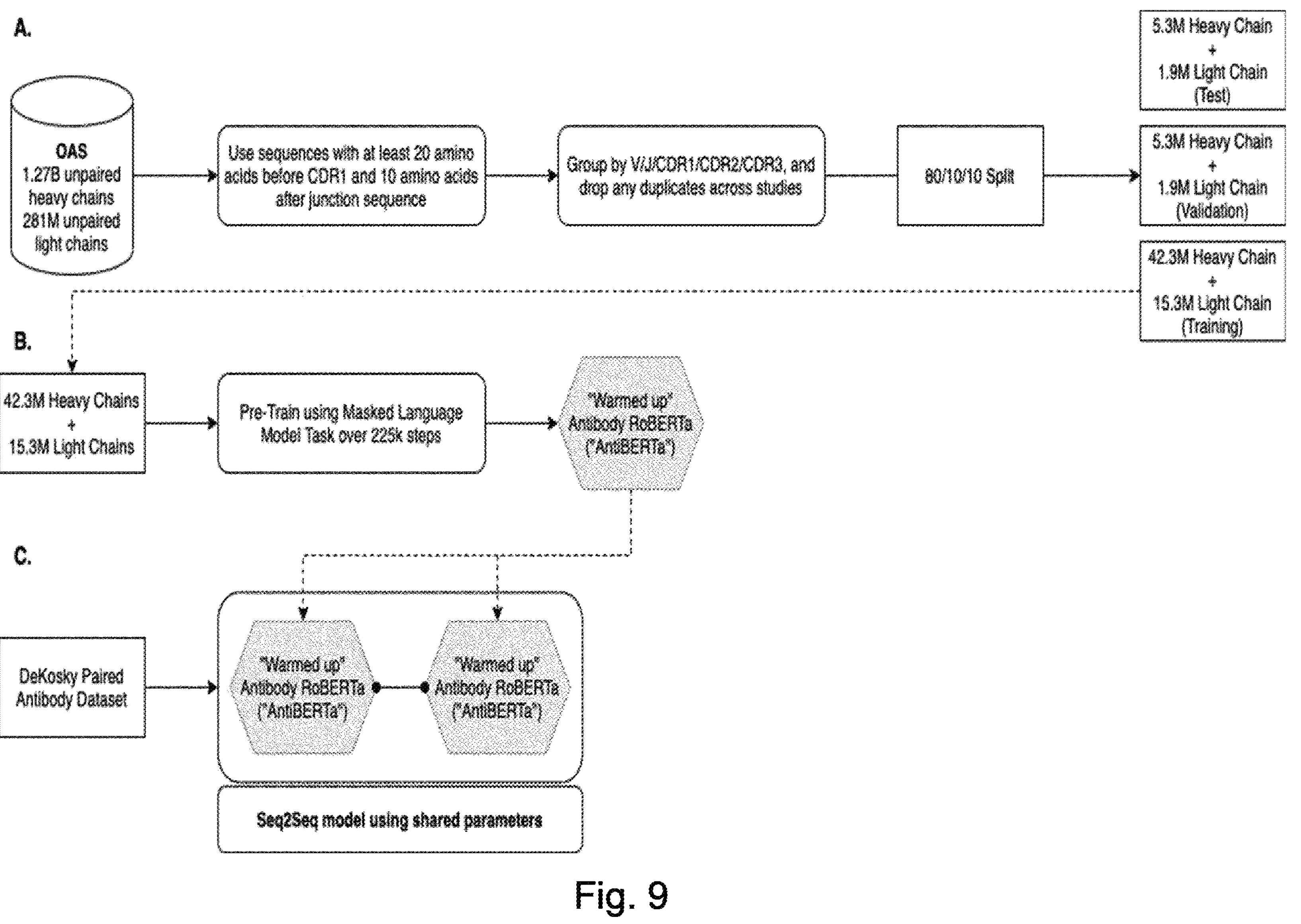
FIG. 9 shows the training procedure for a tandem transformer model as described herein, using two linked AntiBERTa models. A. Creation of the training, validation, and test sets for the masked language model task. B. The set up of the pre-training procedure, and how the "warmed up" model feeds into the subsequent step. C. Outline of how a warmed-up model can be used as part of a Seq2Seq model for NMT.

In addition to the 5 light chain pairing approaches described above, another approach that is able to leverage further training data was designed. In particular, a tandem transformer model was built comprising two RoBERTa models [Liu et al., 2019; Rothe et al., 2020] pre-trained on (full-length) BCR heavy and light chain sequences, respectively (approximately 42.3 million heavy chain sequences and 15.3 million light chain sequences). Unlike Matchmaker and the GRU model, this model was trained using each amino acid as a token, thus allowing complete coverage of sequences. This pre-trained RoBERTa model trained on unpaired antibody sequences is referred to herein as "AntiBERTa", and the training procedure is described in FIG. 9. The AntiBERTa model was trained in a similar style to RoBERTa-base (Liu et al., 2019), but with a smaller batch size of 768, a peak learning rate of $10^{-4}$, and over 225000 pre-training steps and 10000 warm-up steps. For predictions, beam search (Sustkever et al., 2014) was used with a beam width of 3.

The two AntiBERTa models were joined as a sequence-to-sequence model, where the encoder and decoder were each initialised as a copy of the AntiBERTa model using the Huggingface transformers library [Wolf et al., 2019]. The AntiBERTa-AntiBERTa model was then fine-tuned with a slightly larger dataset of paired sequences than what we was used for MatchMaker and the GRU model as described above. In particular, the training data was expanded by introducing more sequences from antigen-experienced libraries (from the same sources as explained above, i.e. DeKosky et al. 2016 and DeKosky et al., 2015). In total, there were 171984 paired sequences. However, as before, the dataset here does not contain the full heavy chain and full light chain sequence. Thus, full sequences were inferred using their germline V and J gene annotations. For the fine-tuning step, the model was trained over 20 epochs, with a peak learning rate of $3\times10^{-5}$ and a 5% warmup. Parameters were shared between the encoder AntiBERTa and the decoder AntiBERTa.

The use of pretrained so called "checkpoints" has been shown to be a powerful strategy in the context of NLP [Rothe et al., 2020]. In particular, a BERT-to-BERT architecture was shown to perform well for NMT in Rothe et al. [2020]. Having demonstrated that approaching the problem of heavy-light chain pairing as a NMT problem using a transformer model (see below), the inventors hypothesised that a BERT-to-BERT architecture would likely also perform very well, and that a RoBERTa-RoBERTa architecture may further improve on this as the RoBERTa model was also shown to improve upon the BERT model for various NLP tasks.

As the paired training data used to train the full model (including the pre-trained AntiBERTa models) does not include full-length BCR heavy and light chain sequences (as described above), an equivalent paired data set that includes full-length sequences is generated using one of two alternative approaches. In a first approach, a full-length sequence is obtained by replacing the V and J gene identifiers with their corresponding germline sequences. In a second approach, the pre-trained AntiBERTa models (or any other such "checkpoint" model sucg as e.g. a GPT-2 model) are used to predict the full-length sequence of the training set, independently for the heavy and light chains (using the respective models) based on the known parts of the chains. The prediction from the "checkpoint" models may be obtained using some or all of the known parts of the chain (e.g. gene segment identifiers, partial sequences etc.), optionally in combination with some information obtained from the germline sequences of any segment for which a full sequence is not available (such as e.g. the identity of some of the amino acids of the segment, for example the first k amino acids of the segment, where k can for example be 1, 2, 3, 5, 10, etc). In other words, the AntiBERTa model trained on the unpaired full-length heavy and light chain data may be used to predict the full-length sequence of the heavy chains in the training data from the V gene identifier, J gene identifier and junction sequence provided in the data. Similarly, the AntiBERTa model trained on the unpaired full-length heavy and light chain data may be used to predict the full-length sequence of the light chains in the training data from the V gene identifier, J gene identifier and junction sequence provided in the data. The same two approaches could be used to map any limited paired training data into data in a more extended format that may have been available to train the "checkpoint" models. Alternatively, the data used to train the "checkpoint" models may be converted to a limited format that matches the format of the paired training data. This may still benefit from the potential additional information gathered by the pre-trained models from the vast number of unpaired sequences available. However, it may not take full advantage of the extent of information available in such unpaired sequence data.

Results

NLP-Inspired Models Generate Light Chains Using Only Heavy Chains as Input

Figure 5:
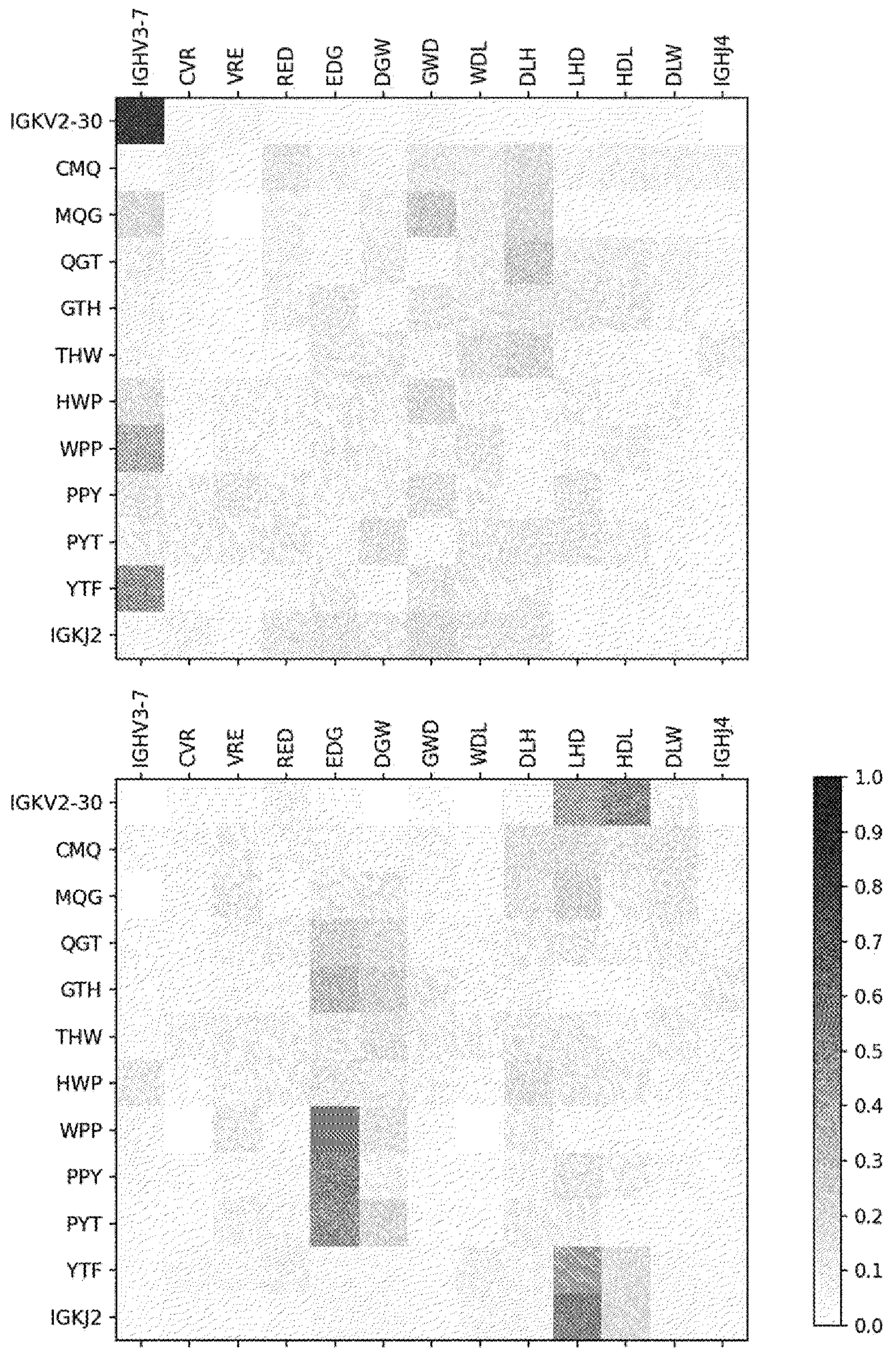
FIG. 5 shows attention heatmaps of heavy chain input and the light chain prediction from a transformer model as described herein. Each column corresponds to an input heavy chain token, and each row represents an output light chain token. Four out of 8 attention heads are shown, showing how each head focuses on different tokens of the heavy chain.
Figure 5:
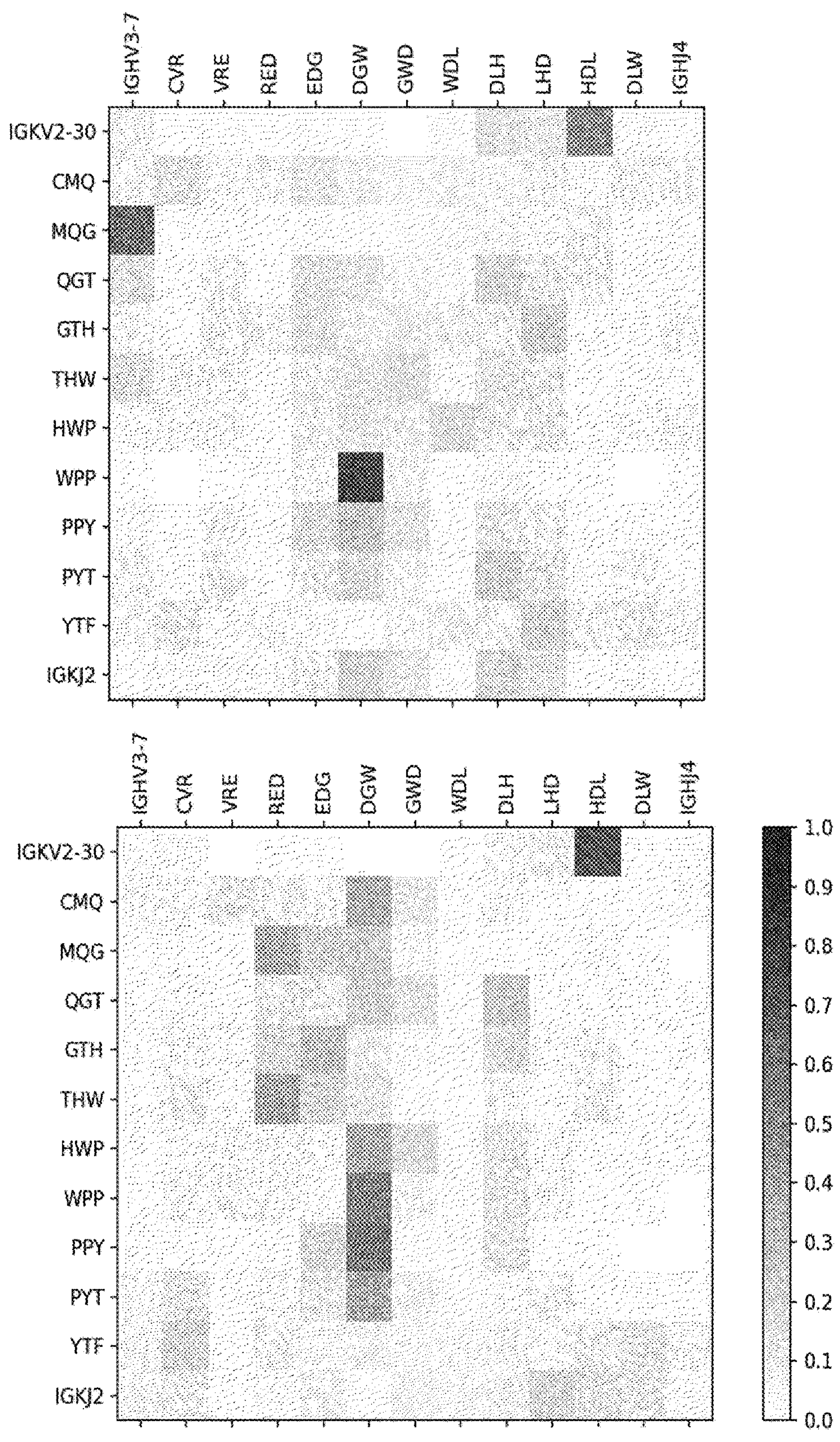

The problem of heavy-light chain pairing was framed as an NMT task, where a light chain sequence is predicted given only the heavy chain sequence as input. Specifically, a Seq2Seq Transformer similar to [Vaswani et al., 2017] was implemented. The model was trained on a tokenised representation of heavy chain sequences as input and returns a tokenised representation of light chain sequences as output, as described in the Methods (FIG. 3A). For an input heavy chain sequence, the model encoder layers compute self-attention between the V-gene, overlapping junction k-mers, and the J-gene. The encoder's self-attention scores on the heavy chain sequence are then used by the decoder to autoregressively predict the light chain sequence. An example of the decoder attention is shown in FIG. 5, where each attention head focuses on different subsets of heavy chain tokens to determine the output light chain tokens.

FIG. 6 shows the prediction performance on the held-out test set and single-cell blind tests for all methods, in terms of light chain V-gene prediction. The V-gene results are investigated separately from the full prediction results because the V-gene forms the largest part of the chain portion determining antigen binding and thus should have a large influence on stability and, to some extent binding (the latter being also strongly influenced by the junction sequence). The light chain V-gene prediction results are further discussed below. The number of correct full light chains, consisting of the V-gene, junction amino acid sequence, and the J-gene, was much lower than the number of correct V-genes across all methods. The full set of prediction results are in Tables 3 and 4.

TABLE 3

| Number of correct light chain V-gene prediction predictions | | | | | | |
|---|---|---|---|---|---|---|
| | Matchmaker | Database | GRU | Frequency | Random | Total |
| Test | 2431 | 4940 | 1786 | 658 | 915 | 18803 |
| Eccles | 64 | 55 | 53 | 26 | 38 | 730 |
| King | 2671 | 2345 | 2119 | 686 | 1224 | 29785 |
| Setliff | 470 | 323 | 434 | 143 | 220 | 4797 |

TABLE 4

| Number of correct light chain V-gene + Junction amino acid sequence + J-gene predictions | | | | | | |
|---|---|---|---|---|---|---|
| | Matchmaker | Database | GRU | Frequency | Random | Total |
| Test | 139 | 1162 | 44 | 12 | 11 | 18803 |
| Eccles | 7 | 4 | 2 | 1 | 2 | 730 |
| King | 105 | 59 | 44 | 0 | 1 | 29785 |
| Setliff | 23 | 6 | 44 | 0 | 3 | 4797 |

Out of 18999 sequences in the test set, 18803 were predicted by all five prediction methods. The transformer-based model predicted the correct light chain V-gene for 2431 heavy chain sequences (12.9%), while the GRU model had 1786 correct predictions (9.5%). The use of the self-attention mechanism in the transformer means that the transformer model should be able to better leverage information on the heavy chain sequence, compared to the GRU model. This likely at least partially explains the higher performance of the transformer-based model compared to the GRU model. The frequency rank-based prediction method had the poorest prediction (658 correct V-genes; 3.5%), which was worse than randomly picking a light chain from the database (915 correct V-genes; 4.9%).

Figure 6A:
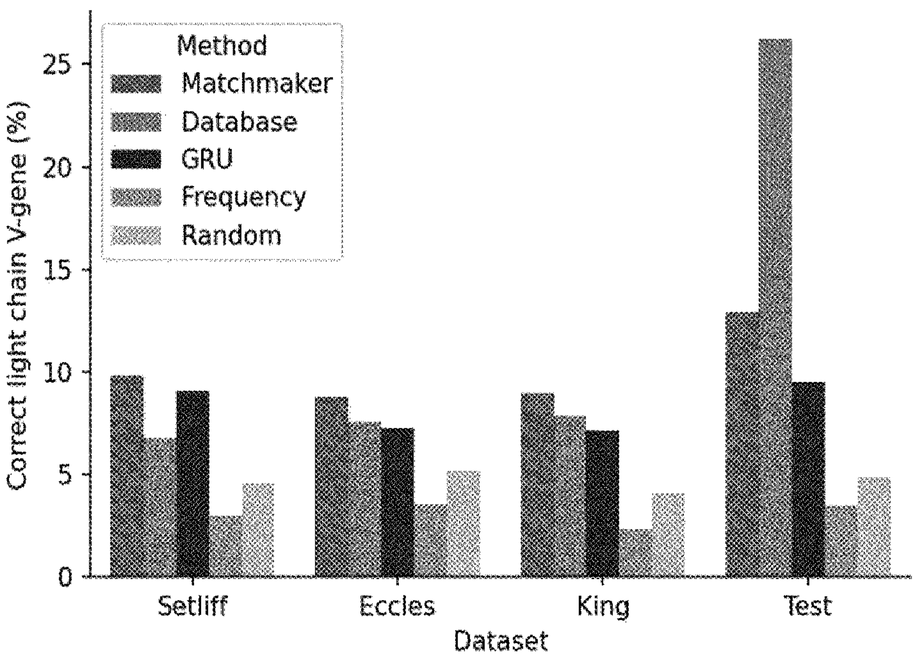
FIG. 6 shows the prediction performance on the held-out test set, and single-cell blind tests, for the methods illustrated on FIG. 3. A: proportion of predictions with the correct light chain V-gene. B: Levenshtein distance distribution of predicted light chain junction sequences on the King et al. [2021] dataset. The Levenshtein distance is a metric that quantifies how different the predicted light chain junction amino acid sequence is with respect to the original. Higher distances mean poorer predictions.

The database search method was the most accurate, with 4940 correct V-genes (26.3%; FIG. 6A). However, as can be seen on FIG. 6A, the database search method did not perform as well in the single-cell blind tests as it did in the test set. In fact, the transformer-based model outperformed the database search method on all single-cell blind tests. The higher performance of the database search method in the test set is believed to be due largely to the presence of clonal relatives in the training and test sets, which is not the case in the blind sets. Indeed, members of a single B cell clone were partitioned across the training and test sets (see Table 5). For example, out of 18803 heavy-light pairs for which prediction was made, 897 had an identical heavy chain sequence to the training set. When allowing for up to one mismatch in the junction amino acid sequence, 3178 sequences were found in the test set that were related to heavy chains in the training set. Among these, 729 (23%) were paired with identical light chain sequences. These are more likely to be accurately paired by the database search method, whereas the redundancy in the heavy chain repertoire in the training set could complicate the task of the NLP-inspired models (akin to requiring a translation model to learn to translate from language A to language B, where a plurality of sentences in language A translate to a single sentence in language B). This bias in the evaluation using the test data could be mitigated by not splitting clones across the training and test sets, i.e. ensuring that members of the same B cell clone (cluster) are not separated between the training and test sets.

TABLE 5

| Example of clonally related sequences in the training and test sets | | | | | |
|---|---|---|---|---|---|
| Dataset | Heavy V-gene and J-gene | Heavy chain junction | Light V-gene and J-gene | Light chain junction | Donor |
| Training | IGHV1-18:IGHJ6 | CARATGAL YYYMDVW | IGLV1-51:IGLJ2 | CGAWDSSL SVVVF | Donor 1, DeKosky et al. 2015 |
| Test | IGHV1-18:IGHJ6 | CARATGAL YYYMDVW | IGLV1-51:IGLJ2 | CGTWDSSL SVVVF | Donor 1, DeKosky et al. 2015 |
| Training | IGHV4-34:IGHJ3 | CARGRGQ GGYPGLFV W | IGKV3-20:IGKJ2 | CQQYGSSP SYTF | Donor 2, DeKosky et al., 2015 |
| Test | IGHV4-34:IGHJ3 | CARGRGLG GYPGLFVW | IGKV3-20:IGKJ2 | CQQYGSSP SYTF | Donor 2, DeKosky et al., 2015 |

Thus, the evaluation on the test set gives a skewed view of the performance of the database search method which would only be realistic if the amount of paired sequence data available to perform such searches was truly representative of the expected diversity of the BCR repertoire (which is far from being the case in reality). In other words, the evaluation on the blind tests gives a much more realistic view of the comparative performance of the methods.

To rule out the impact of clonal relatives across the training and test datasets, the inventors validated Matchmaker in silico using known paired sequences from single-cell datasets in the Paired OAS database [Eccles et al., 2020; King et al., 2021; Setliff et al., 2019]. Since there are no shared individuals between any of these blind test datasets with our training set, any overlapping heavy chain sequences are likely to be public sequences, rather than members of the same B cell clone. None of the heavy chain sequences in the datasets from Eccles et al. [2020] and Setliff et al. [2019] were matched to the training set, while 16 heavy chain sequences in the King et al. [2021] dataset were identical to the training set. The 0.05% overlap in heavy chain sequences is broadly in line with previous observations of heavy chain convergence [Briney et al., 2019].

Across the three single-cell datasets, Matchmaker was the top performer, with up to 9.8% heavy chain sequences being predicted with the correct light chain V-gene (FIG. 6A). Matchmaker was also able to predict the correct light chain V-gene, junction sequence, and J-gene for 105, 7, and 23 heavy chains in the King, Eccles, and Setliff datasets, respectively (Table 4). In comparison, the database search method had 59, 4, and 6 correct predictions. While the GRU model was not as accurate as Matchmaker, it still outperformed the database search method on two single-cell datasets. These results show that deep learning models, especially in scenarios where there are novel heavy chain sequences, can be more useful for light chain prediction. The results further show that the advantages of the deep learning models over other approaches are even more striking when looking at the full-length sequence than when looking only at the V-gene sequence.

Thus, the data on FIG. 6A and Tables 3-4 indicates that the two machine-learning based methods (and the custom-designed database search method) all vastly outperformed a method akin to the prior art (frequency-based search). Amongst these, the transformer-based method showed the best performance across all blind test datasets, a performance advantage that was even more striking when looking at full-length sequences. Both machine learning-based methods also outperformed the database search method on two of the three blind test datasets.

Figure 6B:
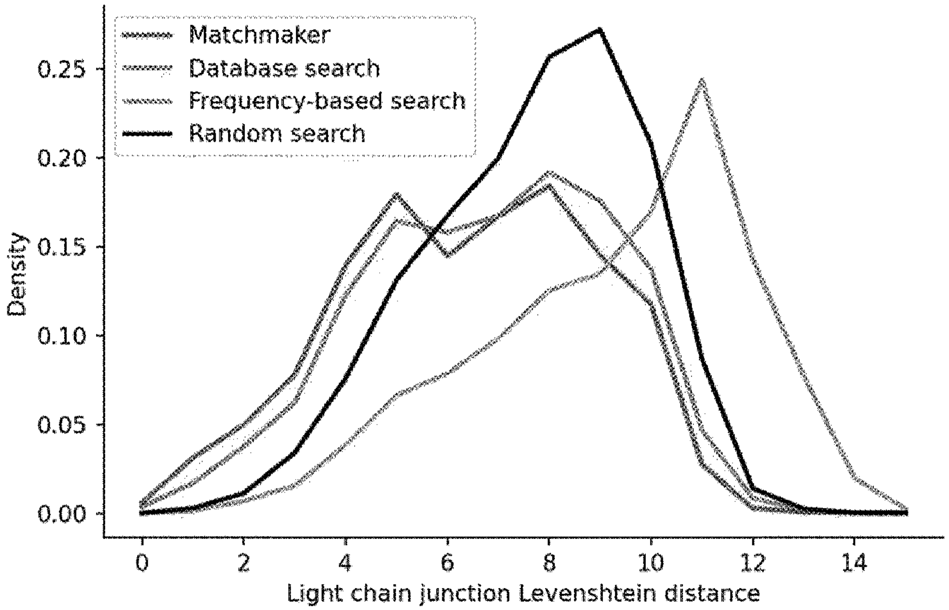
Figure 7:
FIG. 7 shows a schematic representation of the contacts between the native pertuzumab light chain (yellow) and heavy chain (white); PDB: 1s78. At the centre of the image, the alanine is shown in ball-and-stick; an asparagine with the larger side chain, as Matchmaker predicted, may have caused clashes, leading to no expression.

FIG. 6B shows the Levenshtein distance distribution of predicted light chain junction sequences on the King et al. [2021] dataset. This shows that the transformer-based method (Matchmaker) has more predictions with lower distances than any other method, indicating that even if the predicted light chain junction amino acid sequence is not entirely correct, it tends to be closer than with any other method.

Interestingly, for the King et al. [2021] dataset, Matchmaker generated 29 light chain sequence predictions that were not in its training set; two of these had the correct light chain V-gene. However, for these novel light chains, the light chain junction sequence was poorly predicted. The average Levenshtein distance between the 29 predicted light chain junction amino acid sequences and the true amino acid sequences was 8 amino acids.

Experimental Validation

Due to practical limitations, only the best performing machine-learning based method described above (Matchmaker) and the database search method were experimentally validated. As a final validation of the methodology, these methods were used to predict the light chain for 9 therapeutic antibodies (Table 6). These 9 were chosen as the targets are well-established, with the heavy chain playing a varying level of influence on antigen binding. This was quantified by calculating the buried surface area of the heavy chain by inspecting the molecular structures of the native antibodies available in the Protein Data Bank. This information was only available for 8/9 antibodies in the table. For cetuximab, which is derived from a mouse rather than human, the closest human V-gene and J-gene was inferred using ANARCI [Dunbar and Deane., 2016].

TABLE 6

Comparison of native light chain to predicted light chain for the 9 known antibodies.

| Therapeutic mAb | Target | Native | Matchmaker | Database search |
|---|---|---|---|---|
| Trastuzumab | Her2 | IGKV1-39 - IGKJ1 | IGLV2-14 - IGLJ2 | IGKV1-5 - IGKJ1 |
| Pertuzumab | Her2 | IGKV1-33 - IGKJ1 | IGKV1-39 - IGKJ1 | IGKV1-8 - IGKJ3 |
| Cetuximab | EGFR | IGKV6-21 - IGKJ2 | IGKV3-15 - IGKJ4 | IGKV1-39 - IGKJ4 |
| Panitumumab | EGFR | IGKV1-33 - IGKJ4 | IGKV1-33 - IGKJ2 | IGKV1-5 - IGKJ1 |
| Pembrolizumab | PD1 | IGKV3-11 - IGKJ4 | IGLV3-1 - IGLJ2 | IGLV3-19 - IGLJ2 |
| Nivolumab | PD1 | IGKV3-11 - IGKJ1 | IGKV1-33 - IGKJ2 | IGKV2-30 - IGKJ4 |
| Durvalumab | PDL1 | IGKV3-20 - IGKJ1 | IGKV1-39 - IGKJ1 | IGKV1-33 - IGKJ3 |
| Atezolizumab | PDL1 | IGKV1-12 - IGKJ1 | IGKV3-20 - IGKJ3 | IGKV3-20 - IGKJ2 |
| Gemtuzumab | CD33 | IGKV1-5 - IGKJ1 | IGKV3-20 - IGKJ2 | IGLV2-14 - IGLJ1 |

All nine light chain predictions from database search yielded a stable antibody, while one of the nine Matchmaker pairings failed and one was not tested as it initially could not be expressed (see Table 7). Except for the Matchmaker-paired form of nivolumab, all other antibodies from either method produced antibodies that were thermostable. Pertuzumab with the light chain from Matchmaker (IGKV1-39) could be expressed but the pairing did not bind its target, despite its similarity to the native light chain (IGKV1-33). However, there are a few positions at the heavy-chain interface that are different between the prediction and the native light chain sequence. For example, the native pertuzumab light chain has an alanine at position L40, while the Matchmaker-predicted light chain had an asparagine. Thus, both methods (database search and transformer-based predictions) were able to produce stable pairs in most or all cases. Based on the comparatively low performance of the prior art inspired frequency-based method (which as mentioned above performed worse than a random database search), this is likely to be a better result than could have been obtained using a frequency-based method.

TABLE 7

Thermostability relative to native pairing. = same or within 1° C. difference.

| Therapeutic mAb | Target | Native | Matchmaker | Database search |
|---|---|---|---|---|
| Trastuzumab | Her2 | = | = | = |
| Pertuzumab | Her2 | = | Not tested | = |
| Cetuximab | EGFR | = | = | = |
| Panitumumab | EGFR | = | = | = |
| Pembrolizumab | PD1 | = | = | = |
| Nivolumab | PD1 | = | Reduced | = |
| Durvalumab | PDL1 | = | = | = |
| Atezolizumab | PDL1 | = | = | = |
| Gemtuzumab | CD33 | = | = | = |

Figure 8:
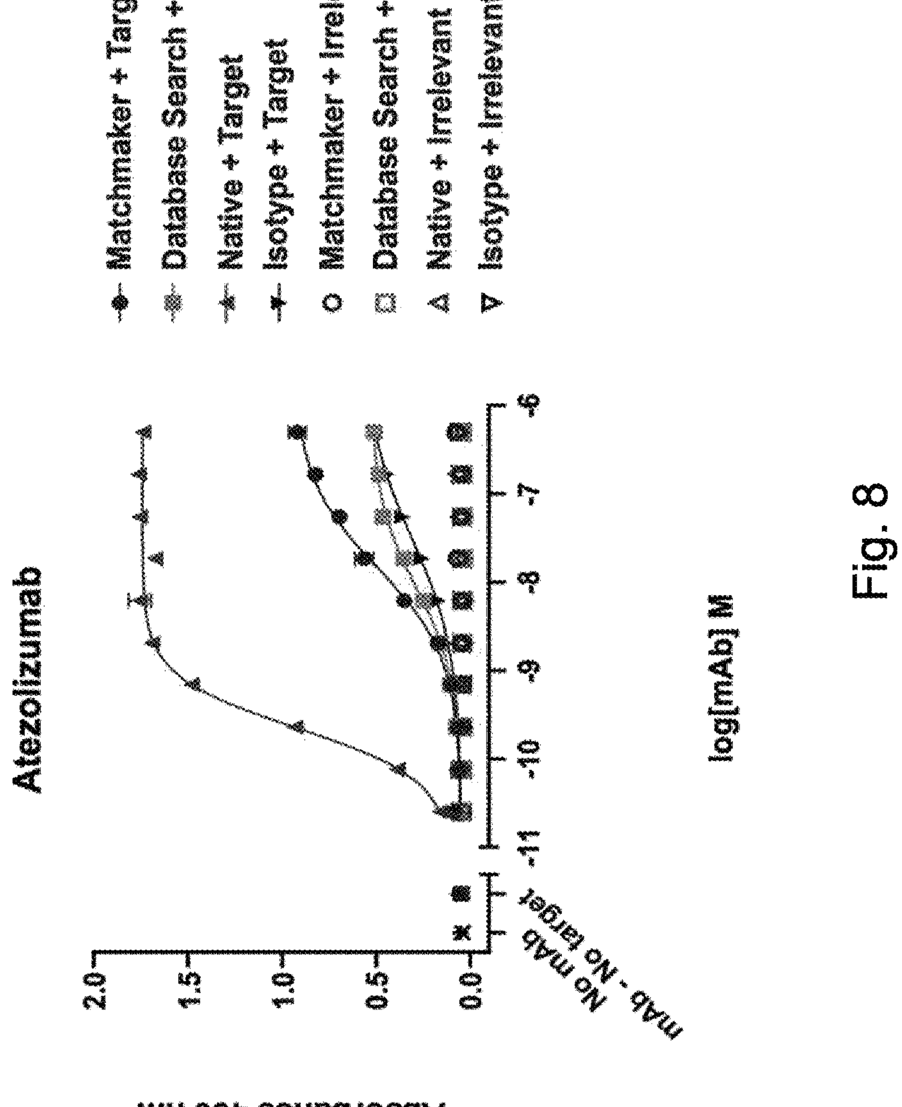
FIG. 8 shows the ELISA Trace for binding of atezolizumab. The filled points represent binding curves for the different antibodies against the target, while unfilled points represent binding against an irrelevant antigen.

Each of the 27 antibodies (9 native, 9 Matchmaker, 9 database) were tested by indirect ELISA for binding to their respective antigens. None of the predictions had a sequence identical to the true sequence and hence none had recovered the full binding affinity of the original antibody. This is expected as the sequences of these therapeutic antibodies is the result of intense engineering for optimised affinity (sometimes not based on sequences of human origin), while the prediction methods are based on naturally occurring sequences. However, the Matchmaker-paired antibodies showed signs of binding for 3/9 cases, while the antibodies made by database searching showed binding for 1/9 (Table 8, FIG. 8). Thus, the data demonstrates that the Matchmaker method is able to generate a significant proportion of pairs that show sufficient binding affinity to form a good basis for further engineering, a step that was until now a significant bottleneck in the process of providing functional antibodies from bulk sequencing of BCR repertoires.

Further, it is expected that the performance of the method could be further enhanced using additional training data reflecting how mutated and/or engineered antibody sequences, such as the therapeutic antibodies used here, are paired. In other words, expanding the training data to enable the model to learn from more data and/or from data comprising sequences that have been optimised is expected to even further improve the ability of the model to predict functional pairings for native as well as engineered antibodies.

TABLE 8

Binding relative to native pairing.

| Therapeutic Antibody | Target | Native | Matchmaker | Database Search | VH contribution to interaction |
|---|---|---|---|---|---|
| Trastuzumab | Her2 | +++++ | − | − | + |
| Pertuzumab | Her2 | +++++ | − | ++++ | +++++ |
| Cetuximab | EGFR | +++++ | + | − | ++ |
| Panitumumab | EGFR | +++++ | − | − | ++ |
| Pembrolizumab | PD1 | +++++ | − | − | ++ |
| Nivolumab | PD1 | +++++ | + | − | +++ |
| Durvalumab | PDL1 | +++++ | − | − | ++ |
| Atezolizumab | PDL1 | +++++ | ++ | − | ++++ |
| Gemtuzumab | CD33 | +++++ | − | − | No structure available, cannot be determined |

Interestingly, Matchmaker predicted the correct light chain V-gene for panitumumab, but the synthesised antibody showed no binding. This highlights that even predicting the correct V-gene does not necessarily rescue the function of the BCR. In fact, none of the pairings predicted by Matchmaker or the database search method that did show binding had the correct V-gene prediction. The determinants of functional antibody pairs are poorly understood. As mentioned above, as the V-gene forms a large part of the binding region, identifying the correct V-gene provides an indication that the pairing is likely to be stable, and at least a promising starting point for identifying binders. However, an incorrect junction can strongly influence the ultimate binding affinity of the pairing, resulting in binding even in the presence of a slightly different V-gene or conversely resulting in no binding even in the presence of the correct V-gene. These results, combined with those on FIGS. 6A and B and Table 4, indicate that the machine-learning based approaches described herein are able to learn complex features that underlie stability and binding, involving a complex interplay between the different parts of the light chain sequence (where exact V-gene sequence matches may not result in as good a binding affinity as a non-exact match combined with a more appropriate junction sequence). This ability, while not perfect, clearly outperforms the newly described non-deep learning based method (database searching) when assessed experimentally. Further, the results from the in-silico investigations indicate that the machine-learning based approaches described herein would outperform a state-of-the-art frequency-based approach by an even greater margin.

The strongest binder among the predictions from Matchmaker was the pertuzumab heavy chain paired with the database light chain. However, pertuzumab's interaction is driven predominantly by the heavy chain, which may indicate that any stable light chain can enable binding. In contrast, Matchmaker's light chains for nivolumab and cetuximab led to binders, despite the relatively lower importance of the heavy chain.

As an additional validation and proof of the clinical utility of the methods described herein, the Matchmaker model described above was used to identify heavy-light chain pairings for heavy chain sequences identified in COVID-19 patients as having a high likelihood of being involved in the immune response, and binding to the coronavirus spike protein. In particular, 18 heavy chain sequences identified from COVID-19 patients as having these properties selected from the data in Galson et al. (2020) were provided as inputs to the method for pairing with light chains. The pairings were expressed and tested for binding to Wuhan strain spike antigens using Homogeneous Time Resolved Fluorescence (HTRF). All 18 antibodies successfully expressed, and 9 of the 18 antibodies were confirmed as binding to Spike protein (where binding was defined as Delta F %>100, the Delta F representing the percent increase in the fluorescent readout compared to a negative control). Thus, 50% of the Matchmaker predictions results in functional antibodies.

Tandem Transformer Model

The structure of the GRU-based and transformer-based models described above impose some limitations on the amount of training data available, as paired heavy-light chain data is required for training. This type of data is available in relatively limited amounts, and is further limited in its content by providing V and J-gene identifiers instead of full sequences (thereby effectively limiting the prediction to the germline sequences for these sections). In order to get around these limitations, a model comprising two transformers that are each trained on much bigger datasets of unpaired heavy chain sequences and light chain sequences (42.3 million and 15.3 million sequences respectively) was built. The results of this are shown in Table 9. While the V gene prediction results were slightly lower than MatchMaker, the number of correct predictions with the correct V-gene, junction amino acid sequence, and J-gene were higher (compare Table 9 and Tables 5, 6). This data shows that this machine-learning based method also outperformed a method akin to the prior art (frequency-based search). The data further shows that the tandem transformer approach has the potential to further improve on the transformer-based method at least when looking at performance over full-length sequences, where the transformer-based approach already showed a striking performance advantage compared to other methods. The performance of this approach is likely to increase even further with additional training data and training time (which was limited here for practical reasons).

TABLE 9

| Number of correct light chain V-gene predictions | | | |
|---|---|---|---|
| | Tandem AntiBERTa Correct V | Tandem AntiBERTa Correct V-gene + Junction amino acid sequence (CDRL3) + J-gene | Total |
| Eccles | 52 (7.8%) | 6 | 741 |
| King | 2559 (8.4%) | 180 | 30327 |
| Setliff | 380 (7.7%) | 37 | 4944 |

Discussion

This example describes a machine-learning, NLP-inspired approach to the problem of BCR heavy-light chain pairing. In particular, two architectures that consider the problem of BCR heavy-light chain pairing as an NMT task are described: Matchmaker, a Seq2Seq Transformer model, and a Seq2Seq GRU-based model. To our knowledge, the present work is the first application of a deep artificial neural networks (ANNs), and in particular Seq2Seq models, for pairing BCR heavy chains, which only requires the heavy chain sequence as input. Matchmaker is the first application of a Transformer model for this purpose. The deep-learning based approach described herein provides the benefit of covering the BCR repertoire as deeply as possible, while also eliminating the need for bulk light chain sequencing. Further, the approach is capable of learning general features of pairings from a set of training data and to use this learning to predict pairings for previously unseen chains. By contrast, an approach such as a database search approach is likely to quickly breakdown when looking at query chains that are not present or more distant from chains that are in known pairings. This is likely to be advantageous in many cases considering the extreme diversity of the BCR repertoire, but particularly so in the context of applications such as identifying specific antibodies that may underlie a desired phenotype in an individual, or other rare antibodies.

The approach was benchmarked against several alternative strategies. On the held-out test set of heavy-light chain pairs, both deep ANNs (and Matchmaker in particular) performed reasonably well, while the database search method had the highest accuracy. Given that relatives of the same B cell clone were found across our training and held-out test sets, it is not surprising that the database search method had the highest accuracy. In fact, it is arguable that obtaining a sufficiently large knowledge base of heavy-light chain pairs, if that was a realistic prospect, would help identify the correct light partner. However, the blind tests showed that when a related heavy chain sequence was not available, database searching had poor accuracy. Frequency searching had the worst performance across all the test scenarios, and even random selection was found to be slightly better. This was lower than expected, and confirms the limitations of using light chain frequencies as a means for pairing.

An interesting observation on the blind test was that Matchmaker was able to predict completely novel light chains; i.e., the predicted light chain sequences were not in the training data. This was also the case for the GRU model which predicted 1 novel light chain, with a fairly low Levenshtein distance to the true sequence (distance=4). While only 29/29785 heavy chains had had a novel light chain prediction by Matchmaker, this suggests that the deep learning models have learned some rules of heavy-light chain pairing by their attention mechanisms, as opposed to memorising the training set. With more higher quality data comprised of full heavy and light chain sequences, we expect deep ANN models such as Matchmaker to learn improved determinants of heavy-light chain pairings. Considering those rules, Matchmaker should generate other novel light chains that are more accurate than those observed in this work.

On a set of nine positive control therapeutic antibodies that were experimentally validated, Matchmaker produced more binders than the database search method. None of the predicted antibodies from either strategy were as potent the native antibody, and most predictions did not lead to binders, which highlights the difficulty of the problem. Variations in binding strength seemed to reflect the heavy chain's contribution to binding, though Matchmaker did not seem to be as affected by these differences. While the precise relationship between the light chain and binding remains unclear, the fact that Matchmaker generates binding antibodies gives a start for further antibody engineering opportunities. In other words, the method is able to predict binders for a proportion of heavy chains, and represents a significant improvement over the prior art at least because (a) it only requires the heavy chain sequence as input, (b) it is not limited in terms of type of sequences and datasets that it can use as input (i.e. it is expected to be able to provide useful predictions for any type of sequence and not only for highly abundant sequences within clonally dominated samples), and (c) it has a higher binder prediction hit rate than other methods (even a method newly described herein that was shown to have a better prediction performance than the state of the art). Any such binder that is successfully obtained thus represents an improvement over the prior art and can be used as a promising starting point for further affinity improvement. Further validation using heavy chain sequences from COVID-19 patients indicates that the performance of Matchmaker may be even higher than indicated based on the limited set of therapeutic antibodies tested as 50% (9/18) of the pairings generated in this data showed some binding to target. The observed improvement compared to comparative methods is not only significant in itself, it is particularly significant when considering that identifying functional heavy-light chain pairings is an extremely complex problem considering the diversity of the BCR repertoire such that any improvement that gets us to sufficient viable candidates for further development is extremely significant in practice. This may be particularly the case in the context of applications such as therapeutic antibody discovery from samples from subjects, where even a small improvement in search efficiency (and this is far from small), will translate into faster results and/or a reduction in wasted effort and resource in discovering, testing, optimising and developing a therapeutic antibody. Further, the models were trained using a training set of 153889 heavy-light chain pairs, which is very small compared to the datasets typically used to train transformer-based models (usually in the order of millions of sequences).

Several possible improvements to the implementation of Matchmaker are envisaged. For instance, the model described above predicts tokens in a greedy fashion (i.e. one token at a time, in other words the most likely token for each individual position is predicted). Using strategies that consider multiple positions at the same time (for example, 3), such as beam search [Sustkever et al., 2014] should help to increase prediction accuracy because the model explores more solutions and is thus less likely to get "stuck" in a suboptimal solution. This is the approach that as used for the tandem transformer model described above. Additionally, the Matchmaker and GRU models exemplified above use a combination of overlapping fixed size k-mers and gene identifiers for the encoding of BCR sequences. The use of single amino acids, or byte-pairs of amino acids as tokens is expected to further improve the model. For example, the tandem transformer model described above used a single token for each amino acid. Using byte-pair encoding, several non-overlapping amino acids are encoded as tokens using a dictionary that is defined automatically in a data-driven manner.

A limitation of the training set is the lack of full-length heavy and light chain sequences. Indeed, such data is currently only available in limited amounts and thus larger datasets comprising only the J-gene identifier, V-gene identifier and junction sequences were used. An alternate tokenisation scheme was designed to address this gap, though it effectively only predicts germline light chain sequences for the V and J-genes (as that is all the information that is available in training data). Since the CDRL1 and CDRL2 loops can form contacts with the CDRH3 [Leem et al., 2016], the predicted light chains may miss any mutant amino acids that form vital interactions with the CDRH3 in vivo. This may be overcome by using different paired heavy-light chain data for training, providing full-length sequences, such as for example data based on cell barcoding such as from the 10× Genomics platform. This may also be addressed using the tandem transformer approach described above where a model can be trained using a combination of larger training data sets of unpaired full-length sequences (to train the checkpoint models) and smaller paired data sets with potentially less extensive sequence coverage.

In order to apply bulk heavy chain repertoire analyses to antibody discovery, the issue of light chain pairing remains pertinent. The deep learning-based approach described herein is unique in its sole dependence on the heavy chain as input. In particular, the Matchmaker (transformer-based) model had the highest in silico accuracy based on multiple metrics and was validated in vitro to generate functional antibodies. This puts Matchmaker in a unique position to predict light chains where paired light chain information is not available. This approach thus has the potential to fill gaps in light chain pairing information, thus enabling therapeutic antibody discovery and a better understanding of the immune system.

Finally, while the approach was described in the context of identifying a light chain pairing for a heavy chain query, it is also applicable to the reverse problem of identifying a heavy chain pairing for a light chain query. This is a less frequent problem as heavy chain sequencing is more common and the heavy chain is believed to play a more important part in determining specificity and affinity.

REFERENCES

Vander Heiden et al., 2017. Dysregulation of B Cell Repertoire Formation in Myasthenia Gravis Patients Revealed through Deep Sequencing. J Immunol. 2017 Feb. 15; 198(4):1460-1473.

Bashford-Rogers et al, 2019. Analysis of the B cell receptor repertoire in six immune-mediated diseases. Nature volume 574, pages 122-126(2019).

Nielsen et al., 2020. Human B Cell Clonal Expansion and Convergent Antibody Responses to SARS-CoV-2. bioRxiv. Preprint. 2020 Jul. 9. doi: 10.1101/2020.07.08.194456.

Simonich et al., 2019. Kappa chain maturation helps drive rapid development of an infant HIV-1 broadly neutralizing antibody lineage. Nature Communications volume 10, Article number: 2190 (2019).

Krawczyk et al., 2019. Looking for therapeutic antibodies in next-generation sequencing repositories. mAbs. Volume 11, 2019—Issue 7, Pages 1197-1205.

Galson et al., 2020. Deep Sequencing of B Cell Receptor Repertoires From COVID-19 Patients Reveals Strong Convergent Immune Signatures. Front. Immunol., 15 Dec. 2020. doi.org/10.3389/fimmu.2020.605170.

Mora and Walczak, 2019. How many different clonotypes do immune repertoires contain? Current Opinion in Systems Biology. Volume 18, December 2019, Pages 104-110

Kovaltsuk et al., 2018. Observed Antibody Space: A Resource for Data Mining Next-Generation Sequencing of Antibody Repertoires. J Immunol Oct. 15, 2018, 201 (8) 2502-2509.

Tiller et al., 2013. A fully synthetic human Fab antibody library based on fixed VH/VL framework pairings with favorable biophysical properties. MAbs. 2013 May 1; 5(3): 445-470.

Teplyakov et al., 2016. Structural diversity in a human antibody germline library. MAbs. August-September 2016; 8(6):1045-63.

Glanville et al., 2009. Precise determination of the diversity of a combinatorial antibody library gives insight into the human immunoglobulin repertoire. PNAS Dec. 1, 2009 106 (48) 20216-20221.

Jayaram et al., 2012. Germline VH/VL pairing in antibodies. Protein Engineering, Design and Selection, Volume 25, Issue 10, October 2012, Pages 523-530.

Ling et al., 2018. Effect of VH-VL Families in Pertuzumab and Trastuzumab Recombinant Production, Her2 and FcγllA Binding. Front. Immunol., 12 Mar. 2018. doi.org/10.3389/fimmu.2018.00469

DeKosky et al., 2013. High-throughput sequencing of the paired human immunoglobulin heavy and light chain repertoire. Nature Biotechnology volume 31, pages 166-169(2013).

DeKosky et al., 2015. In-depth determination and analysis of the human paired heavy- and light-chain antibody repertoire. Nature Medicine volume 21, pages 86-91 (2015).

DeKosky et al., 2016. Large-scale sequence and structural comparisons of human naive and antigen-experienced antibody repertoires. PNAS May 10, 2016 113 (19) E2636-E2645.

King et al., 2021. Single-cell analysis of human B cell maturation predicts how antibody class switching shapes selection dynamics. Science Immunology 12 Feb. 2021. Vol. 6, Issue 56, eabe6291

Eccles et al., 2020. T-bet+ Memory B Cells Link to Local Cross-Reactive IgG upon Human Rhinovirus Infection. Cell Reports Volume 30, Issue 2, 14 Jan. 2020, Pages 351-366.e7

Setliff et al., 2019. High-Throughput Mapping of B Cell Receptor Sequences to Antigen Specificity. Cell Volume 179, Issue 7, 12 Dec. 2019, Pages 1636-1646.e15

Reddy et al., 2010. Monoclonal antibodies isolated without screening by analyzing the variable-gene repertoire of plasma cells. Nature Biotechnology volume 28, pages 965-969(2010).

Zhu et al., 2013. Mining the antibodyome for HIV-1-neutralizing antibodies with next-generation sequencing and phylogenetic pairing of heavy/light chains. PNAS. 2013 Apr. 16; 110(16):6470-5.

Raybould et al., 2021. Public Baseline and shared response structures support the theory of antibody repertoire functional commonality. PLoS Comput Biol 17(3): e1008781.

Rakocevic et al., 2021. The landscape of high-affinity human antibodies against intratumoral antigens. bioRxiv. 8 Feb. 2021. doi.org/10.1101/2021.02.06.430058

Vaswani et al., 2017. Attention Is All You Need. arXiv: 1706.03762

Devlin et al., 2019. BERT: Pre-training of Deep Bidirectional Transformers for Language Understanding. arXiv: 1810.04805

Radford et al., 2019. Language Models are Unsupervised Multitask Learners. https://openai.com/blog/better-language-models/Liu et al., 2019. RoBERTa: A Robustly Optimized BERT Pretraining Approach. arXiv: 1907.11692

Rothe et al., 2020. Leveraging Pre-trained Checkpoints for Sequence Generation Tasks. arXiv:1907.12461

Bahdanau et al., 2015. Neural machine translation by jointly learning to align and translate. arXiv:1409.0473

Cho et al., 2014. Empirical Evaluation of Gated Recurrent Neural Networks on Sequence Modeling. arXiv: 1412.3555

Child et al., 2019. Generating Long Sequences with Sparse Transformers. arXiv:1904.10509

Xiong et al., 2020. On Layer Normalization in the Transformer Architecture. arXiv:2002.04745

Dunbar and Deane, 2016. ANARCI: antigen receptor numbering and receptor classification. Bioinformatics. 2016 Jan. 15; 32(2):298-300.

Sutskever et al., 2014. Sequence to Sequence Learning with Neural Networks.arXiv:1409.3215

Rees, 2020. Understanding the human antibody repertoire. MAbs. January-December 2020; 12(1):1729683.

Leem et al., 2016. ABodyBuilder: Automated antibody structure prediction with data-driven accuracy estimation. MAbs. 2016 October; 8(7):1259-1268.

Ye et al., 2013. IgBLAST: an immunoglobulin variable domain sequence analysis tool. Nucleic Acids Res. 2013 July; 41 (Web Server issue):W34-40.

Furcy, David. Koenig, Sven. "Limited Discrepancy Beam Search". IJCAI'05: Proceedings of the 19th international joint conference on Artificial intelligence. July 2005 Pages 125-131.

Zhou, Rong. Hansen, Eric. "Beam-Stack Search: Integrating Backtracking with Beam Search". Conference: Proceedings of the Fifteenth International Conference on Automated Planning and Scheduling (ICAPS 2005), Jun. 5-10, 2005.

Wolf et al., 2019. HuggingFace's Transformers: State-of-the-art Natural Language Processing. arXiv:1910.03771

Carter Jason A., Preall Jonathan B., Grigaityte Kristina, Goldfless Stephen J., Jeffery Eric, Briggs Adrian W., Vigneault Francois, Atwal Gurinder S. "Single T Cell Sequencing Demonstrates the Functional Role of αβ TCR Pairing in Cell Lineage and Antigen Specificity." Frontiers in Immunology. Vol. 10. 2019, p. 1516. Zheng GXY, Terry J M, Belgrader P, Ryvkin P, Bent Z W, Wilson R, et al. Massively parallel digital transcriptional profiling of single cells. Nat Commun. (2017) 8:14049.

Howie B, Sherwood A M, Berkebile A D, Berka J, Emerson R O, Williamson D W, et al. High-throughput pairing of T cell receptor α and β sequences. Sci Transl Med. (2015) 7:301ra131.

Eve Richardson, Jacob D. Galson, Paul Kellam, Dominic F. Kelly, Sarah E. Smith, Anne Palser, Simon Watson & Charlotte M. Deane (2021) A computational method for immune repertoire mining that identifies novel binders from different clonotypes, demonstrated by identifying anti-pertussis toxoid antibodies, mAbs, 13:1.

Yi-Chun Hsiao, Yonglei Shang, Danielle M. DiCara, Angie Yee, Joyce Lai, Si Hyun Kim, Diego Ellerman, Racquel Corpuz, Yongmei Chen, Sharmila Rajan, Hao Cai, Yan Wu, Dhaya Seshasayee & Isidro Hötzel (2019) Immune repertoire mining for rapid affinity optimization of mouse monoclonal antibodies, mAbs, 11:4, 735-746.

Warszawski S, Borenstein Katz A, Lipsh R, Khmelnitsky L, Ben Nissan G, Javitt G, et al. (2019) Optimizing antibody affinity and stability by the automated design of the variable light-heavy chain interfaces. PLoS Comput Biol 15(8): e1007207.

Seeliger D, Schulz P, Litzenburger T, Spitz J, Hoerer S, Blech M, Enenkel B, Studts J M, Garidel P, Karow A R. Boosting antibody developability through rational sequence optimization. MAbs. 2015; 7(3):505-15. doi: 10.1080/19420862.2015.1017695.

Mason, D. M., Friedensohn, S., Weber, C. R. et al. Optimization of therapeutic antibodies by predicting antigen specificity from antibody sequence via deep learning. Nat Biomed Eng (2021).

Galson Jacob D., Schaetzle Sebastian, Bashford-Rogers Rachael J. M., Raybould Matthew I. J., Kovaltsuk Aleksandr, Kilpatrick Gavin J., Minter Ralph, Finch Donna K., Dias Jorge, James Louisa K., Thomas Gavin, Lee Wing-Yiu Jason, Betley Jason, Cavlan Olivia, Leech Alex, Deane Charlotte M., Seoane Joan, Caldas Carlos, Pennington Daniel J., Pfeffer Paul, Osbourn Jane. Deep Sequencing of B Cell Receptor Repertoires From COVID-19 Patients Reveals Strong Convergent Immune Signatures. Frontiers in Immunology. Vol. 11, 2020.

All references cited herein are incorporated herein by reference in their entirety and for all purposes to the same extent as if each individual publication or patent or patent application was specifically and individually indicated to be incorporated by reference in its entirety.

The specific embodiments described herein are offered by way of example, not by way of limitation. Various modifications and variations of the described compositions, methods, and uses of the technology will be apparent to those skilled in the art without departing from the scope and spirit of the technology as described. Any sub-titles herein are included for convenience only and are not to be construed as limiting the disclosure in any way.

The methods of any embodiments described herein may be provided as computer programs or as computer program products or computer readable media carrying a computer program which is arranged, when run on a computer, to perform the method(s) described above.

Unless context dictates otherwise, the descriptions and definitions of the features set out above are not limited to any particular aspect or embodiment of the invention and apply equally to all aspects and embodiments which are described.

Throughout the specification and claims, the following terms take the meanings explicitly associated herein, unless the context clearly dictates otherwise. The phrase "in one embodiment" as used herein does not necessarily refer to the same embodiment, though it may. Furthermore, the phrase "in another embodiment" as used herein does not necessarily refer to a different embodiment, although it may. Thus, as described below, various embodiments of the invention may be readily combined, without departing from the scope or spirit of the invention.

It must be noted that, as used in the specification and the appended claims, the singular forms "a," "an," and "the"

include plural referents unless the context clearly dictates otherwise. Ranges may be expressed herein as from "about" one particular value, and/or to "about" another particular value. When such a range is expressed, another embodiment includes from the one particular value and/or to the other particular value. Similarly, when values are expressed as approximations, by the use of the antecedent "about," it will be understood that the particular value forms another embodiment. The term "about" in relation to a numerical value is optional and means for example +/−10%.

Throughout this specification, including the claims which follow, unless the context requires otherwise, the word "comprise" and "include", and variations such as "comprises", "comprising", and "including" will be understood to imply the inclusion of a stated integer or step or group of integers or steps but not the exclusion of any other integer or step or group of integers or steps.

Other aspects and embodiments of the invention provide the aspects and embodiments described above with the term "comprising" replaced by the term "consisting of" or "consisting essentially of", unless the context dictates otherwise. "and/or" where used herein is to be taken as specific disclosure of each of the two specified features or components with or without the other. For example "A and/or B" is to be taken as specific disclosure of each of (i) A, (ii) B and (iii) A and B, just as if each is set out individually herein.

The features disclosed in the foregoing description, or in the following claims, or in the accompanying drawings, expressed in their specific forms or in terms of a means for performing the disclosed function, or a method or process for obtaining the disclosed results, as appropriate, may, separately, or in any combination of such features, be utilised for realising the invention in diverse forms thereof.

The invention claimed is:

1. A method of providing an antigen-binding protein comprising a pair of chains, the method comprising:

providing to a processor a query sequence comprising a first chain sequence, and identifying, by said processor, a corresponding chain sequence, thereby identifying an antigen-binding protein comprising the first chain sequence and corresponding chain sequence, wherein said identifying is performed by said processor providing the query sequence to a deep learning model configured to take as input a query first chain sequence and to produce as output at least one corresponding chain sequence, thereby identifying a corresponding chain sequence for the query sequence, wherein the deep learning model has been trained using training first and corresponding chain sequences from known chain pairs; and providing, by said processor, the identified corresponding sequence, a part thereof or information derived therefrom, to a user through a user interface.

2. The method of claim 1, wherein the antigen-binding protein comprises:

(i) a heavy-light chain pair, wherein the first chain sequence is a heavy chain sequence or a light chain sequence, and the corresponding chain sequence is a light chain sequence or a heavy chain sequence, optionally wherein the first chain sequence is a heavy chain sequence and the corresponding sequence is a light chain sequence; or (ii) an αβ chain pair, wherein the first chain sequence is a β chain sequence or an α chain sequence, and the corresponding chain sequence is an α chain sequence or a β chain sequence, optionally wherein the first chain sequence is a β chain sequence and the corresponding sequence is an α chain sequence; or (ii) a γδ chain pair, wherein the first chain sequence is a δ chain sequence or a γ chain sequence, and the corresponding chain sequence is a γ chain sequence or a δ chain sequence, optionally wherein the first chain sequence is a δ chain sequence and the corresponding sequence is a γ chain sequence.

3. The method of claim 1, wherein the deep learning model is a sequence-to-sequence model, and/or wherein the deep learning model comprises a recurrent neural network or a transformer, and/or wherein the deep learning model is a sequence-to-sequence transformer-based model.

4. The method of claim 1, wherein the deep learning model is configured to produce as output one or more corresponding chain sequences, optionally wherein each corresponding chain sequence is associated with a confidence metric such as a probability.

5. The method of claim 1, wherein the training first and corresponding chain sequences from known chain pairs comprise paired training heavy and light chain sequences from single B cell sequencing data, or wherein the training first and corresponding chain sequences from known chain pairs comprise paired training α and β chain sequences from single T cell sequencing data.

6. The method of claim 1, wherein:

(i) the query chain sequence comprises or consists of:

a V-gene sequence or identifier, a J-gene sequence or identifier, and a junction sequence, and optionally a D-gene sequence or identifier; and the corresponding chain sequence comprises or consists of:

a V-gene sequence or identifier, a J-gene sequence or identifier, and a junction sequence; or (ii) the query chain sequence comprises or consists of:

a V-gene sequence or identifier, a J-gene sequence or identifier, and a junction sequence; and the corresponding chain sequence comprises or consists of:

a V-gene sequence or identifier, a J-gene sequence or identifier, and a junction sequence, and optionally a D-gene sequence or identifier.

7. The method of claim 1, wherein the query sequence comprises or consists of one or more first chain CDR sequence(s), and/or wherein the corresponding sequence comprises or consists of one or more corresponding chain CDR sequence(s), optionally wherein the one or more CDR sequence(s) comprises or consists of a CDR3 sequence.

8. The method of claim 1, wherein all sequences are amino acid sequences.

9. The method of claim 1, wherein providing the query sequence to the deep learning model comprises encoding the query sequence using an encoding scheme and/or identifying the corresponding chain sequence comprises decoding a corresponding sequence output by the deep learning model using an encoding scheme, wherein each encoding scheme is individually selected such that:

each gene sequence identifier corresponds to an individual token, each amino acid corresponds to an individual token, and/or sequences are encoded using tokens that each correspond to an individual k-mer or using byte-pair encoding, optionally wherein each sequence is encoded using overlapping k-mers.

10. The method of claim 9, wherein each encoding scheme has been previously defined based on the content of the training chain sequences.

11. The method of claim 1, wherein the query sequence and/or the corresponding sequence comprise(s) one or more gene sequence identifiers and the method further comprises replacing the one or more gene sequence identifiers by the corresponding germline sequence.

12. The method of claim 3, wherein the deep learning model is a transformer-based model comprising an encoder that has been pre-trained using unpaired training first and/or corresponding chain sequences and a decoder that has been pre-trained using unpaired training corresponding and/or first chain sequences, optionally wherein the unpaired training chain sequences comprise full length sequences for the variable region of the corresponding chain, and/or wherein the unpaired training chain sequences comprise full sequences for the variable region of the first chain.

13. The method of claim 1, wherein the method comprises:

obtaining the query sequence by sequencing a sample comprising genetic material encoding for an antigen-binding molecule comprising the query sequence.

14. The method of claim 1, comprising repeating the method for a plurality of query sequences comprising a first chain sequence, wherein at least one of query sequences has been previously identified as likely to have a desired property.

15. The method of claim 1, further comprising obtaining one or more candidate antigen-binding proteins each comprising the query sequence and the corresponding sequence by synthesising the query sequence and identified corresponding sequence.

16. The method of claim 1, further comprising:

providing, to said processor, training data comprising training first and corresponding sequences from known first and corresponding chain pairs, obtaining a vocabulary for encoding of the training first chain sequences and a vocabulary for encoding of the training corresponding chain sequences; and training the deep learning model to take as input a query first chain sequence and to produce as output at least one corresponding chain sequence, using the training data.

17. A system comprising:

a processor; and a computer readable medium comprising instructions that, when executed by the processor, cause the processor to perform a method of identifying an antigen-binding protein comprising a pair of chains, the method comprising:

receiving, by said processor, a query sequence comprising a first chain sequence, and identifying, by said processor, a corresponding chain sequence, thereby identifying an antigen-binding protein comprising the first chain sequence and corresponding chain sequence, wherein said identifying is performed by said processor providing the query sequence to a deep learning model configured to take as input a query first chain sequence and to produce as output at least one corresponding chain sequence, thereby identifying a corresponding chain sequence for the query sequence, wherein the deep learning model has been trained using training first and corresponding chain sequences from known chain pairs.

18. One or more computer readable media comprising instructions that, when executed by one or more processors, cause the one or more processors to perform a method of identifying an antigen-binding protein comprising a pair of chains, the method comprising:

receiving, by said processor, training data comprising training first and corresponding sequences from known first and corresponding chain pairs;

training, by said processor, a deep learning model to take as input a query first chain sequence and to produce as output at least one corresponding chain sequence, using the training data;

receiving, by said processor, a query sequence comprising a first chain sequence, and identifying, by said processor, a corresponding chain sequence, thereby identifying an antigen-binding protein comprising the first chain sequence and corresponding chain sequence, wherein said identifying is performed by said processor providing the query sequence to the trained deep learning model configured to take as input a query first chain sequence and to produce as output at least one corresponding chain sequence, thereby identifying a corresponding chain sequence for the query sequence.

19. The method of claim 13, wherein obtaining the query sequence comprises performing B cell bulk sequencing of a sample comprising B cells, T cell bulk sequencing of a sample comprising T cells, or bulk sequencing of a sample comprising any other cells expressing an antigen-binding molecule comprising the query sequence, or genetic material derived therefrom, such as a B cell receptor library or a T cell receptor library.

20. The method of claim 15, further comprising testing the one or more candidate antigen-binding proteins in vitro for a desired property.

* * * * *